United States Patent
Chang

(10) Patent No.: US 10,118,033 B2
(45) Date of Patent: *Nov. 6, 2018

(54) SYSTEM AND METHOD FOR REDUCING INFLAMMATION OF TISSUE

(71) Applicant: Wen-Chieh Chang, Taichung (TW)

(72) Inventor: Wen-Chieh Chang, Taichung (TW)

(73) Assignee: Taiwan Resonant Waves Research Corp., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/287,738

(22) Filed: Oct. 7, 2016

(65) Prior Publication Data
US 2018/0099141 A1    Apr. 12, 2018

(51) Int. Cl.
*A61N 1/32*       (2006.01)
*A61N 1/04*       (2006.01)

(52) U.S. Cl.
CPC ............. *A61N 1/32* (2013.01); *A61N 1/0472* (2013.01)

(58) Field of Classification Search
CPC .................. A61N 1/32; A61N 1/0472; A61N 2005/0606; A61N 5/0624; A61C 9/0053
See application file for complete search history.

(56) References Cited

U.S. PATENT DOCUMENTS

| 6,035,236 A * | 3/2000 | Jarding ................... A61N 1/32 607/53 |
| 9,421,368 B2* | 8/2016 | Chang ................ A61N 1/36014 |
| 2017/0172842 A1* | 6/2017 | Chang .................. A61H 23/008 |
| 2017/0312506 A1* | 11/2017 | Chang .................. A61N 1/0492 |

* cited by examiner

*Primary Examiner* — Catherine Voorhees

(57) ABSTRACT

A system and method for reducing inflammation of tissue of animal or human, which comprises an energy wave generator has an energy wave's frequency control mode. The energy wave's frequency control mode includes multiple controls for acting the energy wave generator to generate and emit energy waves each with a corresponding energy density. The energy density is calculated by a corresponding base frequency, a sweep bandwidth of the corresponding base frequency, an emission rate and a total time of emission in a duty cycle, so that the energy waves with the corresponding energy densities effecting on the body of animals or human to reduce inflammation of tissue of animal or human.

20 Claims, 13 Drawing Sheets

| Order | Fo(hz) | D(%) | P(hz) | T(sec) | SF(1) | SD(2) | SI(3) | SC(4) | SE(5) | Width | TT(sec) | BD | Norm | ED | Aveage | filter | Lower limit | Upper limit | <Lower limit | >Upper limit |
|---|---|---|---|---|---|---|---|---|---|---|---|---|---|---|---|---|---|---|---|---|
| 1 | 18122 | 70 | 1 | 7 | 1 | | | | | 0 | 7 | 4.95 | 1.8% | 4.95 | 4.95 | 1 | 2.47 | 6.19 | 1.45 | 8.45 |
| 2 | 10000.0 | 70 | 1 | 15 | 1 | | | | | 0 | 15 | 5.02 | 1.9% | 5.02 | 5.02 | 1 | 2.51 | 6.28 | 1.52 | 8.52 |
| 3 | 7344.0 | 70 | 1 | 19 | 1 | | | | | 0 | 19 | 4.99 | 1.9% | 4.99 | 4.99 | 1 | 2.49 | 6.24 | 1.49 | 8.49 |
| 4 | 5000.0 | 70 | 1 | 24 | 1 | | | | | 0 | 24 | 4.92 | 1.8% | 4.92 | 4.92 | 1 | 2.46 | 6.15 | 1.42 | 8.42 |
| 5 | 4200.0 | 70 | 1 | 26 | 1 | | | | | 0 | 26 | 4.88 | 1.8% | 4.88 | 4.88 | 1 | 2.44 | 6.10 | 1.38 | 8.38 |
| 6 | 3672.0 | 70 | 1 | 28 | 1 | | | | | 0 | 28 | 4.86 | 1.8% | 4.86 | 4.86 | 1 | 2.43 | 6.07 | 1.36 | 8.36 |
| 7 | 3175.0 | 70 | 1 | 10 | | 2 | | | | 2 | 30 | 5.30 | 2.0% | 5.30 | 5.30 | 0 | 0.00 | 0.00 | 1.80 | 8.80 |
| 8 | 3000.0 | 70 | 1 | 31 | 1 | | | | | 0 | 31 | 4.81 | 1.8% | 4.81 | 4.81 | 0 | 0.00 | 0.00 | 1.31 | 8.31 |
| 9 | 2127.0 | 70 | 1 | 18 | | 2 | | | | 1 | 36 | 5.03 | 1.9% | 5.03 | 5.03 | 0 | 0.00 | 0.00 | 1.53 | 8.53 |
| 10 | 2112.0 | 70 | 1 | 35 | 1 | | | | | 0 | 35 | 4.71 | 1.8% | 4.71 | 4.71 | 0 | 0.00 | 0.00 | 1.21 | 8.21 |
| 11 | 2007.0 | 70 | 1 | 2 | | | | 4 | | 7 | 30 | 5.80 | 2.2% | 5.80 | 5.80 | 1 | 2.90 | 7.25 | 2.30 | 9.30 |
| 12 | 1865.0 | 70 | 1 | 37 | 1 | | | | | 0 | 37 | 4.68 | 1.7% | 4.68 | 4.68 | 1 | 2.34 | 5.85 | 1.18 | 8.18 |
| 13 | 1850.0 | 70 | 1 | 37 | 1 | | | | | 0 | 37 | 4.68 | 1.7% | 4.68 | 4.68 | 1 | 2.34 | 5.85 | 1.18 | 8.18 |
| 14 | 1550.0 | 70 | 1 | 39 | 1 | | | | | 0 | 39 | 4.63 | 1.7% | 4.63 | 4.63 | 1 | 2.31 | 5.78 | 1.13 | 8.13 |
| 15 | 1234.0 | 70 | 1 | 42 | 1 | | | | | 0 | 42 | 4.56 | 1.7% | 4.56 | 4.56 | 1 | 2.28 | 5.70 | 1.06 | 8.06 |
| 16 | 1043.0 | 70 | 1 | 44 | 1 | | | | | 0 | 44 | 4.51 | 1.7% | 4.51 | 4.51 | 0 | 0.00 | 0.00 | 1.01 | 8.01 |
| 17 | 1000.0 | 70 | 1 | 45 | 1 | | | | | 0 | 45 | 4.50 | 1.7% | 4.50 | 4.50 | 0 | 0.00 | 0.00 | 1.00 | 8.00 |
| 18 | 921.0 | 70 | 1 | 15 | | | 3 | | | 2 | 45 | 4.94 | 1.8% | 4.94 | 4.94 | 0 | 0.00 | 0.00 | 1.44 | 8.44 |
| 19 | 880.0 | 70 | 1 | 47 | 1 | | | | | 0 | 47 | 4.46 | 1.7% | 4.46 | 4.46 | 0 | 0.00 | 0.00 | 0.96 | 7.96 |
| 20 | 867.0 | 70 | 1 | 23 | | 2 | | | | 1 | 46 | 4.75 | 1.8% | 4.75 | 4.75 | 0 | 0.00 | 0.00 | 1.25 | 8.25 |
| 21 | 807.0 | 70 | 1 | 3 | | | | 4 | | 7 | 45 | 5.58 | 2.1% | 5.58 | 5.58 | 1 | 2.79 | 6.98 | 2.08 | 9.08 |
| 22 | 778.0 | 70 | 1 | 3 | | | | 4 | | 9 | 57 | 5.77 | 2.1% | 5.77 | 5.77 | 1 | 2.89 | 7.21 | 2.27 | 9.27 |
| 23 | 751.0 | 70 | 1 | 49 | 1 | | | | | 0 | 49 | 4.41 | 1.6% | 4.41 | 4.41 | 1 | 2.21 | 5.51 | 0.91 | 7.91 |
| 24 | 730.0 | 70 | 1 | 3 | | | | 4 | | 7 | 45 | 5.54 | 2.1% | 5.54 | 5.54 | 1 | 2.77 | 6.92 | 2.04 | 9.04 |
| 25 | 705.0 | 70 | 1 | 12 | | 2 | | | | 3 | 48 | 4.98 | 1.8% | 4.98 | 4.98 | 0 | 0.00 | 0.00 | 1.48 | 8.48 |
| 26 | 668.0 | 70 | 1 | 6 | | | 3 | | | 8 | 54 | 5.36 | 2.0% | 5.36 | 5.36 | 0 | 0.00 | 0.00 | 1.86 | 8.86 |
| 27 | 652.0 | 70 | 1 | 5 | | | | 4 | | 5 | 55 | 5.44 | 2.0% | 5.44 | 5.44 | 0 | 0.00 | 0.00 | 1.94 | 8.94 |
| 28 | 625.0 | 70 | 1 | 9 | | 2 | | | | 5 | 54 | 5.15 | 1.9% | 5.15 | 5.15 | 0 | 0.00 | 0.00 | 1.65 | 8.65 |
| 29 | 612.0 | 70 | 1 | 51 | 1 | | | | | 0 | 51 | 4.34 | 1.6% | 4.34 | 4.34 | 0 | 0.00 | 0.00 | 0.84 | 7.84 |
| 30 | 595.0 | 70 | 1 | 9 | | | 3 | | | 5 | 54 | 5.13 | 1.9% | 5.13 | 5.13 | 0 | 0.00 | 0.00 | 1.63 | 8.63 |
| 31 | 542.0 | 70 | 1 | 3 | | | | 4 | | 9 | 57 | 5.61 | 2.1% | 5.61 | 5.61 | 1 | 2.81 | 7.02 | 2.11 | 9.11 |
| 32 | 522.0 | 70 | 1 | 53 | 1 | | | | | 0 | 53 | 4.29 | 1.6% | 4.29 | 4.29 | 1 | 2.14 | 5.36 | 0.79 | 7.79 |
| 33 | 484.0 | 70 | 1 | 11 | | | 3 | | | 4 | 55 | 4.97 | 1.8% | 4.97 | 4.97 | 1 | 2.48 | 6.21 | 1.47 | 8.47 |
| 34 | 462.0 | 70 | 1 | 14 | | 2 | | | | 3 | 56 | 4.86 | 1.8% | 4.86 | 4.86 | 1 | 2.43 | 6.07 | 1.36 | 8.36 |
| 35 | 435.0 | 70 | 1 | 6 | | | 3 | | | 9 | 60 | 5.26 | 2.0% | 5.26 | 5.26 | 0 | 0.00 | 0.00 | 1.76 | 8.76 |
| 36 | 421.0 | 70 | 1 | 14 | | 2 | | | | 3 | 56 | 4.82 | 1.8% | 4.82 | 4.82 | 0 | 0.00 | 0.00 | 1.32 | 8.32 |
| 37 | 380.0 | 70 | 1 | 12 | | | 3 | | | 4 | 60 | 4.90 | 1.8% | 4.90 | 4.90 | 0 | 0.00 | 0.00 | 1.40 | 8.40 |
| 38 | 348.0 | 70 | 1 | 5 | | | | 4 | | 5 | 55 | 5.17 | 1.9% | 5.17 | 5.17 | 0 | 0.00 | 0.00 | 1.67 | 8.67 |
| 39 | 302.0 | 70 | 1 | 20 | | 2 | | | | 2 | 60 | 4.58 | 1.7% | 4.58 | 4.58 | 0 | 0.00 | 0.00 | 1.08 | 8.08 |
| 40 | 160.0 | 70 | 1 | 23 | | | 3 | | | 2 | 69 | 4.37 | 1.6% | 4.37 | 4.37 | 0 | 0.00 | 0.00 | 0.87 | 7.87 |
| 41 | 141.0 | 70 | 1 | 5 | | | | 4 | | 6 | 65 | 4.92 | 1.8% | 4.92 | 4.92 | 1 | 2.46 | 6.15 | 1.42 | 8.42 |
| 42 | 125.0 | 70 | 1 | 72 | 1 | | | | | 0 | 72 | 3.80 | 1.4% | 3.80 | 3.80 | 1 | 1.90 | 4.75 | 0.30 | 7.30 |
| 43 | 95.0 | 70 | 1 | 76 | 1 | | | | | 0 | 76 | 3.70 | 1.4% | 3.70 | 3.70 | 1 | 1.85 | 4.63 | 0.20 | 7.20 |
| 44 | 80.0 | 70 | 1 | 39 | | 2 | | | | 1 | 78 | 3.94 | 1.5% | 3.94 | 3.94 | 0 | 0.00 | 0.00 | 0.44 | 7.44 |
| 45 | 66.0 | 70 | 1 | 5 | | | | 4 | | 7 | 75 | 4.72 | 1.8% | 4.72 | 4.72 | 0 | 0.00 | 0.00 | 1.22 | 8.22 |
| 46 | 40.0 | 70 | 1 | 5 | | | | 4 | | 8 | 85 | 4.61 | 1.7% | 4.61 | 4.61 | 0 | 0.00 | 0.00 | 1.11 | 8.11 |
| 47 | 13.0 | 70 | 1 | 7 | | | | 4 | | 7 | 105 | 4.16 | 1.5% | 4.16 | 4.16 | 0 | 0.00 | 0.00 | 0.66 | 7.66 |
| 48 | 9.0 | 70 | 1 | 106 | 1 | | | | | 0 | 106 | 2.83 | 1.0% | 2.83 | 2.83 | 0 | 0.00 | 0.00 | -0.67 | 6.33 |
| 49 | 6.0 | 70 | 1 | 110 | 1 | | | | | 0 | 110 | 2.67 | 1.0% | 2.67 | 2.67 | 1 | 1.33 | 3.33 | -0.83 | 6.17 |
| 50 | 1.0 | 70 | 1 | 133 | 1 | | | | | 0 | 133 | 1.97 | 0.7% | 1.97 | 1.97 | 1 | 0.99 | 2.47 | -1.53 | 5.47 |
| 51 | 28.0 | 70 | 0 | 8 | | 2 | | | | 8 | 72 | 4.10 | 1.5% | 4.10 | 4.10 | 1 | 2.05 | 5.13 | 0.60 | 7.60 |
| 52 | 19.0 | 70 | 0 | 8 | | 2 | | | | 8 | 72 | 3.94 | 1.5% | 3.94 | 3.94 | 0 | 0.00 | 0.00 | 0.44 | 7.44 |
| 53 | 10.0 | 70 | 0 | 8 | | 2 | | | | 2 | 24 | 2.70 | 1.0% | 2.70 | 2.70 | 0 | 0.00 | 0.00 | -0.80 | 6.20 |
| 54 | 7.8 | 70 | 0 | 144 | 1 | | | | | 0 | 144 | 2.90 | 1.1% | 2.90 | 2.90 | 1 | 1.45 | 3.62 | -0.60 | 6.40 |
| 55 | 6.0 | 70 | 0 | 144 | 1 | | | | | 0 | 144 | 2.78 | 1.0% | 2.78 | 2.78 | 1 | 1.39 | 3.48 | -0.72 | 6.28 |
| 56 | 5.0 | 70 | 0 | 144 | 1 | | | | | 0 | 144 | 2.70 | 1.0% | 2.70 | 2.70 | 0 | 0.00 | 0.00 | -0.80 | 6.20 |
| 57 | 6.0 | 70 | 0 | 144 | 1 | | | | | 0 | 144 | 2.78 | 1.0% | 2.78 | 2.78 | 1 | 1.39 | 3.48 | -0.72 | 6.28 |
| 58 | 7.8 | 70 | 0 | 144 | 1 | | | | | 0 | 144 | 2.90 | 1.1% | 2.90 | 2.90 | 1 | 1.45 | 3.62 | -0.60 | 6.40 |
| 59 | 8.0 | 70 | 0 | 4 | | | 3 | | | 8 | 36 | 3.26 | 1.2% | 3.26 | 3.26 | 0 | 0.00 | 0.00 | -0.24 | 6.76 |
| 60 | 17.0 | 70 | 0 | 4 | | | 3 | | | 8 | 36 | 3.59 | 1.3% | 3.59 | 3.59 | 1 | 1.79 | 4.48 | 0.09 | 7.09 |
| 61 | 26.0 | 70 | 0 | 4 | | | 3 | | | 2 | 12 | 2.82 | 1.0% | 2.82 | 2.82 | 1 | 1.41 | 3.52 | -0.68 | 6.32 |

FIG.7

SYSTEM AND METHOD FOR REDUCING INFLAMMATION OF TISSUE

BACKGROUND OF THE INVENTION

1. Fields of the Invention

The present invention relates to a system and method for reducing inflammation of tissue, and more particularly, to a technology for controlling and emitting energy waves to effect on the body of animal or human to reduce inflammation of tissue of animal or human.

2. Descriptions of Related Art

Oral tissue inflammation generally means there is phenomenon of swelling, spots or sores on the mouth, lips or tongue. Among them, more common oral inflammations and diseases are aphthous, cold sores, leukoplakia and oral rosary disease. Oral ulcers and inflammation not only produce sense of pain and discomfort, but also interfere eating and speaking. In the modern medical point of view, anyone with more than one week of continuous oral ulcers must seek for medical attention, and is recommended to check the cause of inflammation by biopsy method, so as to be the basis of determination for excluding serious illnesses such as cancer and AIDS. Moreover, some medical experts believe that the diseases and inflammation of oral tissues are closely related with body's immune system, bacteria, viruses, stress, trauma, allergies, smoking and deficiencies of iron or vitamin.

Different treatment ways for oral inflammation are adapted according to the types of symptoms, in general the common treatments are: 1. using non-prescription ointments, analgesics or anti-bacterial mouthwash, which treatment can provide temporary relief only and may help to reduce the index of inflammation, but can't effectively cure the inflammation; 2. taking prescription antibacterial agents, antifungal agents, or viral drug, which treatment can help to reduce the index of inflammation, and reduce the chance of infection; and 3. using non-prescription topical anesthetics, which although may provide temporary relief, but can't effectively cure the inflammation too.

In addition to the aforementioned treatment, good habit of oral hygiene is also very important factor to avoid oral tissue inflammation. Periodontal disease is one of very common diseases of oral tissues. The main reason for the occurrence of periodontal disease is caused by bacteria invading periodontal tissues of oral, bacteria and bacterial toxin cause destruction and disintegration of the gum, periodontal ligament and alveolar bone, the light symptoms are bad breath, gum swelling and pain redness, and brushing bleeding, and the severe symptoms are shaking of teeth and falling off. Moreover, periodontal disease can infect each other through saliva, once the bacteria of gingival inflammation enters into the blood and attaches to the injured heart valve or endocardial wall, that finally may causes bacterial endocarditis and results in heart disease. Traditional treatments for periodontal disease, surgery is the way to turn the meat gums to scrape out the inside stones and dirt, and flap surgery must be adapted for severe periodontal diseases to open the gum of patient and scrape periodontal necrotic tissue. Another treatment for periodontal diseases is laser treatment. The laser treatment is painless and mainly using the characteristics of sterilization by laser's high-temperature. The physicians can clear the oral bacteria of patient without harming any periodontal tissue. Painless laser treatment has the advantages of reduction of treatment time, less bleeding, less damage and high effectiveness of sterilization. Laser treatment can activate the self-healing and reconstructing capacity of periodontal tissue by laser beam so as to grow its own new organizational structure. Although laser treatment can achieve the purpose of reducing shake and of consolidation of the teeth, the cost of laser treatment is higher than traditional surgery, and the cost is calculated depending on the depth of the periodontal pocket, generally the cost is about 2-3 times that of the traditional treatment.

To apply wave energy in sound, electromagnetic or optical form effecting on plant, animal or human, to promote cell growth, or inhibit the growth of foreign cells, or produce specific physiological or psychological treatment or soothing, is currently quite universally endorsed technology and research. But currently available conventional arts are only roughly using a simple fixed frequency wave energy of simply combination of low and high frequencies to act on the human body, they are not in-depth studied to know and have what kind energy wave with controls of combination of specific different frequencies is effective for corresponding diseases and physical discomfort, and they are only rough frequency energy wave regardless what kind illness or physical discomfort to be applied for, so the effectiveness of treatment or relieve of symptoms must be unable to highlight.

According to the theory of quantum medicine, all living things and life forms have their own physiological frequency (which is the biological resonant wave), and harmonized wave frequency occurs in healthy human bodies. On the other hand, a disordered wave frequency occurred in human body indicates functional degradation of the living thing and sickness caused by a harmonic interference of diseases or viruses. In 1930, American physicist, Royal Rife, discovered that every object contains bacteria and viruses having their own natural frequency, and such discovery was used by doctors of University of Southern California for medical tests in 1934 and satisfactory results were achieved. Royal Rife's research discovered that different resonant energy waves have different physiological reactions to human body. Thereafter, a Canadian corporation, Resonant Light Technology Inc. developed a resonant wave health instrument for measuring the physiological frequency of a human body. The electric energy wave emitted from the instrument has a wavelength of 4~20 microns (um), which is very close to the wavelength of the biological wave of a human body (3~45 um), so as to provide a healthcare function to human body. At present, researches on the subject of treating cancers by electromagnetic waves are conducted extensively. Although the prior art has introduced electric energy waves into human body to produce resonance with the physiological frequency of human body, so as to achieve the treatment effect, yet the conventional techniques or researches do not use the electric energy wave technology to create a frequency modulation treatment formulation for reducing inflammation of tissue of animal and human effectively.

Since the biological resonant energy waves probably have high efficacy in improvement of physiological faculty and curing diseases, and the inventor of the present patent application has researched for a long time to apply the resonant energy wave to improve some kinds of physiological faculty and cure some diseases. The inventor had an invention of system and method for emitting energy wave by specific frequency controls to reduce or eliminate high blood sugar factor of diabetes, and such invention had been issued for Taiwanese patent No. I453046 and U.S. Pat. No. 9,421,368. After the aforementioned invention, the inventor of the present patent application put into research applying serial specific controls of energy wave for alleviating or curing diseases such as the present invention for reducing inflammation of tissue of animal or human.

SUMMARY OF THE INVENTION

The primary objective of the present invention is to provide a system and method for reducing inflammation of tissue of animal or human. The system comprises an energy wave generator having an energy wave's frequency control mode for controlling and generating energy waves. The energy wave's frequency control mode comprises multiple controls in multiple energy wave generation periods respectively. According to the multiple controls the energy wave generator generates and emits energy waves each with a corresponding energy density having a value between 0.99~7.25 by a corresponding base frequency between 1~18150 Hz to effect on bodies of animals or human so as to reduce inflammation of tissue of the animals or human. The control modes are at least one fixed frequency sweep mode and at least one adjusted frequency sweep mode. The energy density of each energy wave is calculated by the following formula: ED=log 10 (freq.×D %×(2Width+1)×(TT)+1), wherein freq., Width, D % and TT represent the base frequency, the predetermined sweep bandwidth, an emission rate and a total time of emission in a duty cycle of the base frequency respectively.

BRIEF DESCRIPTION OF THE DRAWINGS

FIG. 7 is a schematic view of list of relations between spectrums of effect frequencies, modulation parameters and energy densities of the present invention;

DETAILED DESCRIPTION OF THE PREFERRED EMBODIMENT

Figure 1:
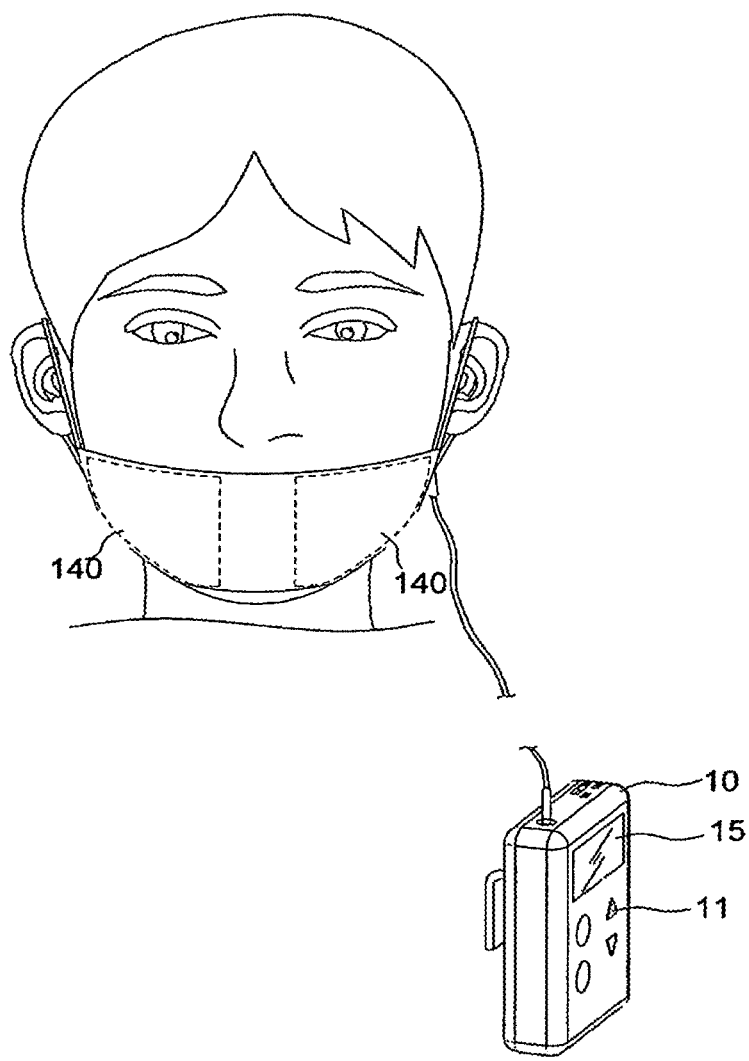
FIG. 1 is a schematic view of the system of the present invention.
Figure 2:
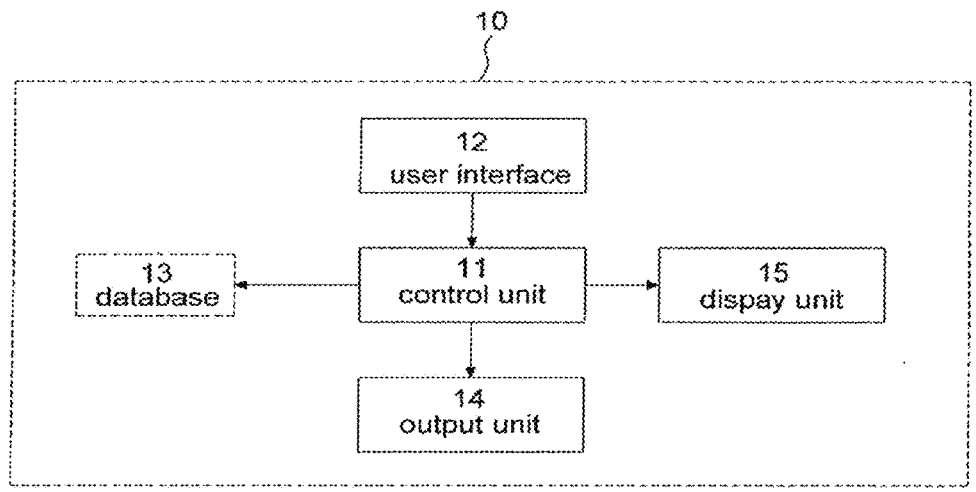
FIG. 2 is a schematic block diagram of units of the system of the present invention.

Referring to FIGS. 1 to 7, the system of the present invention comprises an energy wave generator 10. The energy wave generator 10 is set up with an energy wave's frequency control mode. The energy wave generator 10 generates and emits energy waves (i.e. resonant wave) according to the control of the energy wave's frequency control mode. In one embodiment of the present invention, the energy wave's frequency control mode includes first to ninth sets of controls in corresponding first to ninth sets of energy wave generation periods. The energy wave generator 10 generates and emits the energy waves each with a corresponding energy density by a corresponding frequency sweep mode based on a base frequency in the first to ninth energy wave generation periods respectively according to the controls of the energy wave's frequency control mode, so that the energy waves effect on the body to reduce inflammation of oral tissue. Referring to FIGS. 1 to 2, the energy wave generator 10 comprises a user interface 12, a control unit 11, a database 13 for saving the information of spectrums of effect frequency and modulation parameters corresponding to each effect frequency used in each energy wave generation periods, an energy wave output unit 14 and a display unit 15. In one embodiment of the present invention, the energy waves are in electric forms, and the energy wave output unit 14 includes a set of electrode sheets 140 for affixing to the body of animal or human so as to construct a circulation loop between the body and the electrical energy wave output unit 14 to transmit electric energy waves to the body of animal or human. The control unit 11 (such as a combination of microcontroller and driving circuit) sequentially reads the information of spectrums and modulation parameters of effect frequencies in the database 13, and then drives the energy wave output unit 14 to sequentially generates and emits electric energy waves each with a respective energy density (ED) in each corresponding energy wave generation period.

The control unit 11 of the present invention can be triggered to read the associated information of spectrums and modulation parameters in the database 13 by the command signals generated from the user interface 12, and then generates driving signals to control the energy wave output unit 14 (such as weak pulse generating circuit, 0<voltage≤10V, 0<current≤5 mA) switching on and off according to the corresponding frequencies, so that the energy wave output unit 14 generates corresponding electric energy waves with corresponding energy densities in required distributions of values in the corresponding energy wave generation periods. The display unit 15 is used to display the status of operation or procession of the system. Further, the embodiment of the present invention, the energy wave output unit 14 is not to be limited to a weak pulse generating circuit, the energy wave output unit 14 also may be a light emitting device or an audio play device enabling the energy wave generator system 10 to emits energy waves in light form or audio form in required corresponding frequencies.

In one embodiment of the invention, the energy wave generator 10 according to the control of the energy wave's frequency control mode sequentially outputs the energy waves from first to ninth energy wave generation periods. The controls of the energy wave's frequency control mode are for: (a) continuously and sequentially generating a 1st to a 6th energy waves with a corresponding 1st to a 6th energy densities by a corresponding 1st to a 6th base frequencies respectively in the first energy wave generation period, wherein, the 1st energy density of the 1st energy wave is between 2.47~6.19 (preferably 4.95), the 2nd energy density of the 2nd energy wave is between 2.51~6.28 (preferably 5.02), the 3rd energy density of the 3rd energy wave is between 2.49~6.24 (preferably 4.99), the 4th energy density of the 4th energy wave is between 2.46~6.16 (preferably 4.92), the 5th energy density of the 5th energy wave is between 2.44~6.10 (preferably 4.88), and the 6th energy density of the 6th energy wave is between 2.43~6.07 (preferably 4.86); (b) continuously and sequentially generating a 7th to a 11th energy waves with corresponding a 7th to a 11th energy densities by a 7th to a 11th base frequencies respectively in the second energy wave generation period, wherein, the 7th energy density is between 2.90~7.25 (preferably 5.80), the 8th energy density between 2.34~5.85 (preferably 4.48), the 9th energy density is between 2.34~5.85 (preferably 4.68), the 10th energy density is between 2.31~5.78 (preferably 4.63), the 11th energy density is between 2.28~5.70 (preferably 4.56); (c) continuously and sequentially generating a 12th to a 15th energy waves with a 12th to a 15th energy densities by a 12th to a 15th base frequencies respectively in the third energy wave generation period, wherein, the 12th energy density is between 2.79~6.98 (preferably 5.58), the 13th energy density is between 2.89~7.21 (preferably 5.77), the 14th energy density is between 2.21~5.51 (preferably 4.41), and the 15th energy density is between 2.77~6.92 (preferably 5.54); (d) continuously and sequentially generating a 16th to a 19th energy waves with a 16th to a 19th energy densities by a 16th to a 19th base frequencies respectively in the fourth energy wave generation period, wherein, the 16th energy density is between 2.81~7.02 (preferably 4.34), the 17th energy density is between 2.14~5.36 (preferably 4.29), the 18th energy density is between 2.48~6.21 (preferably 4.97), the 19th energy density is between 2.43~6.07 (preferably 4.86)); (e) continuously and sequentially generating a 20th to a 22nd energy waves with a 20th to a 22nd energy densities by a 20th to a 22nd base frequencies respectively in the fifth energy wave generation period, wherein, the 20th energy density is between 2.46~6.15 (preferably 4.92), the 21st energy density is between 1.90~4.75 (preferably 4.37), the 22nd the energy density is between 1.85 and 4.63 (preferably 3.70); (f) continuously and sequentially generating a 23rd to a 25th energy waves with a 23rd to a 25th energy densities by a 23rd to a 25th base frequencies respectively in the sixth energy wave generation period, wherein, the 23rd energy density is between 1.33~3.33 (preferably 2.67), the 24th energy density is between 0.99~2.47 (preferably 1.97), the 25th energy density is between 2.05~5.13 (preferably 4.10); (g) continuously and sequentially generating a 26th to a 27th energy waves with a 26th to a 27th energy densities by a 26th to a 27th base frequencies respectively in the seventh energy wave generation period, wherein, the 26th energy density is between 1.45~3.62 (preferably 2.90), the 27th energy density is between 1.39~3.48 (preferably 2.78); (h) continuously and sequentially generating a 28th to a 29th energy waves with a 28th to a 29th energy densities by a 28th to a 29th base frequencies respectively in the eighth energy wave generation period, wherein, the 28th energy density is between 1.39~3.48 (preferably 2.78), the 29th energy density is between 1.45~3.62 (preferably 2.90); and (i) continuously and sequentially generating a 30th to a 31st energy waves with a 30th to a 31st energy densities by a 30th to a 31st base frequencies respectively in the ninth energy wave generation period, wherein, the 30th energy density is between 1.79~4.48 (preferably 3.59), and the 31st energy density is between 1.41~3.52 (preferably 2.82).

The value of aforementioned energy densities of the energy waves by their corresponding frequencies are calculated by the formula: $ED = \log 10 \, (freq. \times D\% \times (2Width+1) \times (TT) + 1)$. For example of the 1st base frequency in the first energy wave generation period, if we set the 1st base freq.=18122 Hz, the emission rate in a duty cycle (D %)=70%, the sweep bandwidth (Width) (m)=0 Hz and the total time of emission (TT)=7 secs in a duty cycle, and then the energy density (ED)=$\log 10 \, (18122 \times 70\% \times (2 \times 0+1) \times 7+1)$=4.95. Although there is no specific unit referring to the energy density (ED) of the present invention, the ED has real meaning, which represents a total transmit power of energy wave. When the frequency is higher, the times of switch voltage (current) is more, and energy used is more. The total time of emission means the duration of effect energy wave. The value of ED has been taken into account with all transmission parameters, which is on behalf of transmitting behavior. If each parameter is changed too large, the ED will also change. If the energy density exceeds the scope of the set ones, the efficiency also will be changed with it.

Figure 3:
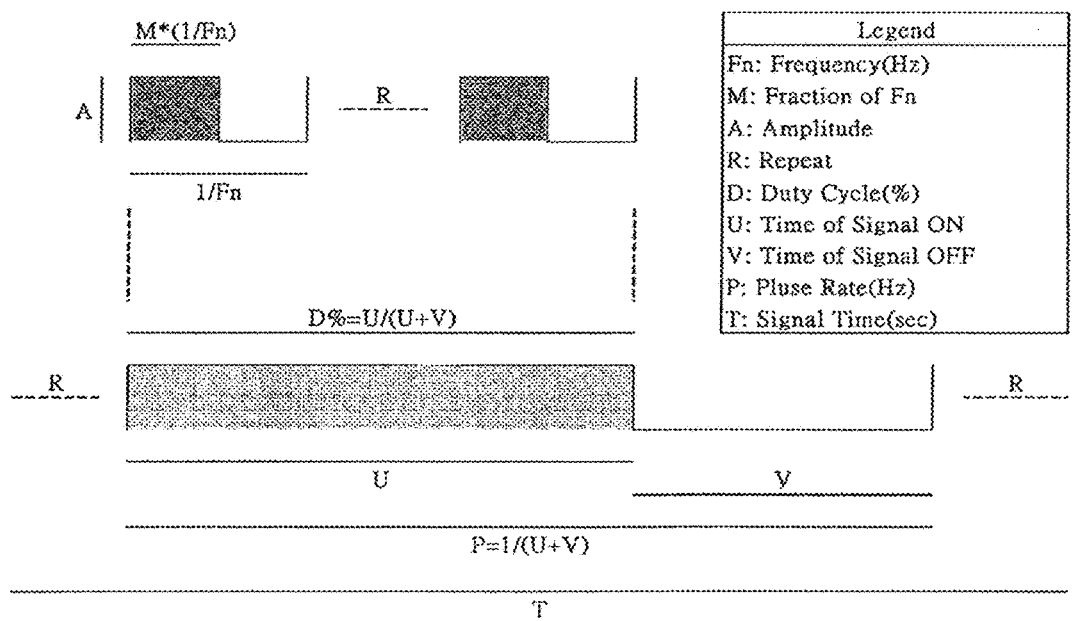
FIG. 3 is a schematic view of wave form of a duty cycle of the present invention.
Figure 4:
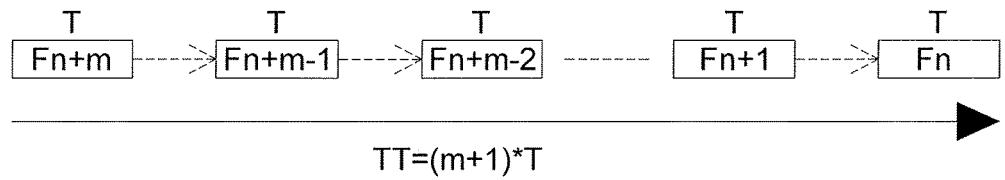
FIG. 4 is a schematic view of distribution of effect frequencies calculated by the sweep decreasing mode of the present invention.

As shown in FIGS. 3 and 7, in one embodiment of the present invention, the energy wave is a square wave, D is the duty cycle, T is effect time of a single frequency, D % is emission rate of duty cycle of each base frequency and equal to $U/(U+V)$. In the embodiment of present invention, we set the wave emission rate to be 70% for each duty cycle. U is the part of 70% which represents the time of signal outputs of positive potential in square wave, and V is the part of 30% which represents the time of signal outputs of 0 potential in OFF status. P represents a Pulse Rate (Hz) of frequency, $P=1/(U+V)$. TT is the total time of emission period based on each base frequency in each duty cycle. In FIG. 4, the normalized percentages (normal) in each order, is the ratio between the ED in the effect period based on each base frequency and the sum of ED of the whole effect periods based on whole base frequencies from order 1 to 61 shown in FIG. 7.

Referring to FIG. 7, during the first energy wave generation period, the control mode of the 1st frequency is fixed frequency sweep mode, which sets a fixed 1st base frequency (freq.) between 18100 Hz~18150 Hz (preferably 18122 Hz), emission rate (D %)=70% for a duty cycle, sweep bandwidth (Width) (m)=0 Hz and total time of emission (TT)=7 seconds for a duty cycle; the control mode of the 2nd frequency is fixed frequency sweep mode, which sets a fixed 2nd base frequency within 9990 Hz~10100 Hz (preferably 10000 Hz), D %=70%, Width (m)=0 Hz and TT=15 secs for a duty cycle; the control mode of the 3rd frequency is fixed frequency sweep mode, which sets a fixed 3rd base frequency within 7300 Hz~7370 Hz (preferably 7344 Hz), D %=70%, Width (m)=0 Hz and TT=19 secs for a duty cycle; the control mode of the 4th frequency is fixed frequency sweep mode, which sets a fixed 4th base frequency within 4990 Hz~5050 Hz (preferably 5000 Hz), D %=70%, Width (m)=0 Hz and TT=24 secs for a duty cycle; the control mode of the 5th frequency is fixed frequency sweep mode, which sets a fixed 5th base frequency within 4100 Hz~4250 Hz (preferably 4200 Hz), D %=70%, Width (m)=0 Hz and TT=26 secs for a duty cycle; and the control mode of the 6th frequency is fixed frequency sweep mode, which sets a fixed 6th base frequency within 3600 Hz~3700 Hz (preferably 3672 Hz), D %=70%, Width (m)=0 Hz and TT=28 secs for a duty cycle.

Referring to FIG. 7, during the second energy wave generation period, the control mode of the 7th frequency is a spread contract mode, which sets effect frequencies decreasing and increasing alternately adjusted to contract based on a 7th base frequency between 2000 Hz~2080 Hz (preferably 2007 Hz) with emission rate (D %) equal to 70%, sweep bandwidth (Width) (m) equal to 7 Hz, adjusted bandwidth equal to 1 Hz and total time of emission (TT) equal to 30 seconds; the control mode of the 8th frequency is a fixed frequency sweep mode, which sets a fixed 8th base frequency between 1800 Hz~1900 Hz (preferably 1865 Hz) with D %=70%, Width (m)=0 Hz and TT=37 secs for a duty cycle; the control mode of the 9th base frequency is a fixed frequency sweep mode, which sets a fixed 9th base frequency between 1830 Hz~1860 Hz (preferably 1850 Hz) with D %=70%, Width (m)=0 Hz and TT=37 secs for a duty cycle; the control mode of the 10th frequency is a fixed frequency sweep mode, which sets a fixed 10th base frequency between 1500 Hz~1590 Hz (preferably 1550 Hz) with D %=70%, Width (m)=0 Hz and TT=39 secs for a duty cycle; and the control mode of the 11th frequency is a fixed frequency sweep mode, which sets a fixed 11th base frequency between 1220 Hz~1250 Hz (preferably 1234 Hz) with D %=70%, Width (m)=0 Hz and TT=42 secs for a duty cycle.

Referring to FIG. 7, during the third energy wave generation period, the control mode of the 12th frequency is a spread contract mode, which sets effect frequencies decreasing and increasing alternately adjusted to contract based on a 12th base frequency between 800 Hz~860 Hz (preferably 807 Hz) with emission rate (D %) equal to 70%, sweep bandwidth (Width) (m) equal to 7 Hz, adjusted bandwidth equal to 1 Hz and total time of emission (TT) equal to 45 seconds; the control mode of the 13th frequency is a spread contract mode, which sets effect frequencies decreasing and increasing alternately adjusted to contract based on a 13th base frequency between 750 Hz~800 Hz (preferably 778 Hz) with emission rate (D %) equal to 70%, sweep bandwidth (Width) (m) equal to 9 Hz, adjusted bandwidth equal to 1 Hz and total time of emission (TT) equal to 57 seconds; the control mode of the 14th frequency is a fixed frequency sweep mode, which sets a fixed 14th base frequency between 700 Hz~790 Hz (preferably 751 Hz) with D %=70%, Width (m)=0 Hz and TT=49 secs for a duty cycle; the control mode of the 15th frequency is a spread contract mode, which sets effect frequencies decreasing and increasing alternately adjusted to contract based on a 15th base frequency between 700 Hz~750 Hz (preferably 730 Hz) with D %=70%, Width (m)=7 Hz, adjusted bandwidth=1 Hz and TT=45 secs for a duty cycle.

Referring to FIG. 7, during the fourth energy wave generation period, the control mode of the 16th frequency is a spread contract mode, which sets effect frequencies decreasing and increasing alternately adjusted to contract based on a 16th base frequency between 500 Hz~580 Hz (preferably 542 Hz) with D %=70%, Width (m)=9 Hz, adjusted bandwidth=1 Hz and TT=57 secs for a duty cycle; the control mode of the 17th frequency is a fixed frequency sweep mode, which sets a fixed 17th base frequency between 510 Hz~550 Hz (preferably 522 Hz) with D %=70%, Width (m)=0 Hz and TT=53 secs for a duty cycle; the control mode of the 18th frequency is a sweep increasing mode, which sets effect frequencies increasingly adjusted based on a 18th base frequency between 470~500 Hz (preferably 484 Hz) with D %=70%, Width (m)=4 Hz, adjusted bandwidth=1 Hz and TT=55 secs for a duty cycle; the control mode of the 19th frequency is a sweep decreasing mode, which sets effect frequencies decreasingly adjusted based on a 19th base frequency between 450~480 Hz (preferably 462 Hz) with D %=70%, Width (m)=3 Hz, adjusted bandwidth=1 Hz and TT=56 secs for a duty cycle.

Referring to FIG. 7, during the fifth energy wave generation period, the control mode of the 20th frequency is a spread contract mode, which sets effect frequencies decreasing and increasing alternately adjusted to contract based on a 20th base frequency between 130 Hz~150 Hz (preferably 141 Hz) with D %=70%, Width (m)=6 Hz, adjusted bandwidth=1 Hz and TT=65 secs for a duty cycle; the control mode of the 21st frequency is a fixed frequency sweep mode, which sets a fixed 21st base frequency between 110~140 Hz (preferably 125 Hz) with D %=70%, Width (m)=0 Hz and TT=72 secs for a duty cycle; and the control mode of the 22nd frequency is a fixed frequency sweep mode, which sets a fixed 22nd base frequency between 80~110 Hz (preferably 95 Hz) with D %=70%, Width (m)=0 Hz and TT=76 secs for a duty cycle.

Referring to FIG. 7, during the sixth energy wave generation period, the control mode of the 23rd frequency is a fixed frequency sweep mode, which sets a fixed 23rd base frequency between 4~10 Hz (preferably 6 Hz) with D %=70%, Width (m)=0 Hz and TT=110 secs for a duty cycle; the control mode of the 24th frequency is a fixed frequency sweep mode, which sets a fixed 24th base frequency between 0.5~10 Hz (preferably 1 Hz) with D %=70%, Width (m)=0 Hz and TT=133 secs for a duty cycle; the control mode of the 25th frequency is a sweep decreasing mode, which sets effect frequencies decreasingly adjusted based on a 25th base frequency between 20~50 Hz (preferably 28 Hz) with D %=70%, Width (m)=8 Hz, adjusted bandwidth=1 Hz and TT=72 secs for a duty cycle.

Referring to FIG. 7, during the seventh energy wave generation period, the control mode of the 26th frequency is a fixed frequency sweep mode, which sets a fixed 26th base frequency between 5~20 Hz (preferably 7.83 Hz) with D %=70%, Width (m)=0 Hz and TT=144 secs for a duty cycle; and the control mode of the 27th frequency is a fixed frequency sweep mode, which sets a fixed 27th base frequency between 5~15 Hz (preferably 6 Hz) with D %=70%, Width (m)=0 Hz and TT=144 secs for a duty cycle.

Referring to FIG. 7, during the eighth energy wave generation period, the control mode of the 28th frequency is a fixed frequency sweep mode, which sets a fixed 28th base frequency between 5~15 Hz (preferably 6 Hz) with D %=70%, Width (m)=0 Hz and TT=144 secs for a duty cycle; and the control mode of the 29th frequency is a fixed frequency sweep mode, which sets a fixed 29th base frequency between 5~20 Hz (preferably 7.83 Hz) with D %=70%, Width (m)=0 Hz and TT=144 secs for a duty cycle.

Referring to FIG. 7, during the ninth energy wave generation period, the control mode of the 30th frequency is a sweep increasing mode, which sets effect frequencies increasingly adjusted based on a 30th base frequency between 10~30 Hz (preferably 17 Hz) with D %=70%, Width (m)=8 Hz, adjusted bandwidth=1 Hz and TT=36 secs for a duty cycle; and the control mode of the 31st frequency is a sweep increasing mode, which sets effect frequencies increasingly adjusted based on a 31st base frequency between 15~40 Hz (preferably 26 Hz) with D %=70%, Width (m)=2 Hz, adjusted bandwidth=1 Hz and TT=12 secs for a duty cycle.

Referring to FIGS. 3 and 7, the fixed frequency sweep mode depicted in the present invention means the frequency of each treatment functioning at a fixed frequency until the total time of the frequency effect period ends. In the case of the first energy wave generation period, for example, assuming that the first frequency is 18122 Hz, then the first frequency is fixed at 18122 Hz until the total time of the frequency reaches 7 seconds. After that, it goes to the next frequency effect period, and so on. Because there is no value change of the frequency range for the fixed frequency sweep mode, therefore, the sweep bandwidth is 0 Hz.

Referring to FIGS. 4 and 7, the control of the aforementioned sweep decreasing mode is to control the system to emit the energy wave by frequency decreasing distribution with an adjusted bandwidth in a predetermined bandwidth. The calculation of the value change of the sweep decreasing mode depicted in the present invention is described as below. The first output frequency is calculated as a base frequency (Fn) plus a sweep bandwidth (m), and the second output frequency is calculated as the first output frequency minus an adjusted bandwidth (such as 1 Hz). When the current output frequency is equal to the base frequency (Fn), the current output frequency will be the last output frequency. In the case of the 25th frequency (freq), the base frequency is 28 Hz with sweep bandwidth (Width) 8 Hz. Based on the above formula, nine frequencies can be obtained, and the sequence of the output frequency is 36 Hz, 35 Hz, 34 Hz, 33 Hz, 32 Hz, 31 Hz, 30 Hz, 29 Hz and 28 Hz respectively. Each single-frequency's effect time (T) in the sweep decreasing mode is 8 seconds, so the total time of the two frequencies (TT) is 72 seconds, i.e., $TT=(m+1)*T$.

Figure 5:
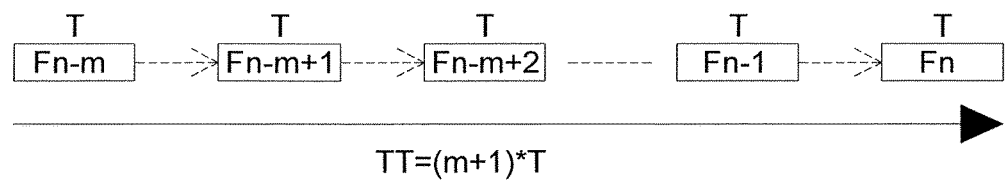
FIG. 5 is a schematic view of distribution of effect frequencies calculated by the sweep increasing mode of the present invention.

Referring to FIGS. 5 and 7, the control of the aforementioned sweep increasing mode is to control the system to emit the energy wave by frequency increasing distribution with an adjusted bandwidth in a predetermined sweep bandwidth. The calculation of the value change of the sweep increasing mode depicted in the present invention is described as below. The first output frequency is calculated as a base frequency (Fn) minus a sweep bandwidth (m), and the second output frequency is calculated as the first output frequency plus an adjusted bandwidth (such as 1 Hz). When the current output frequency is equal to the base frequency (Fn), the current output frequency will be the last output frequency. In the case of the 18th frequency, the base frequency is 484 Hz with sweep bandwidth (Width) (m) 4 Hz and adjusted bandwidth 1 Hz. Based on the above formula, five frequencies can be obtained, and the sequence of the output frequency is 480 Hz, 481 Hz, 482 Hz, 483 Hz and 484 Hz respectively. Each single-frequency's effect time (T) in the sweep increasing mode is 11 seconds, so that the total time of the six frequencies (TT) is 55 seconds, i.e., $TT=(m+1)*T$.

Figure 6:
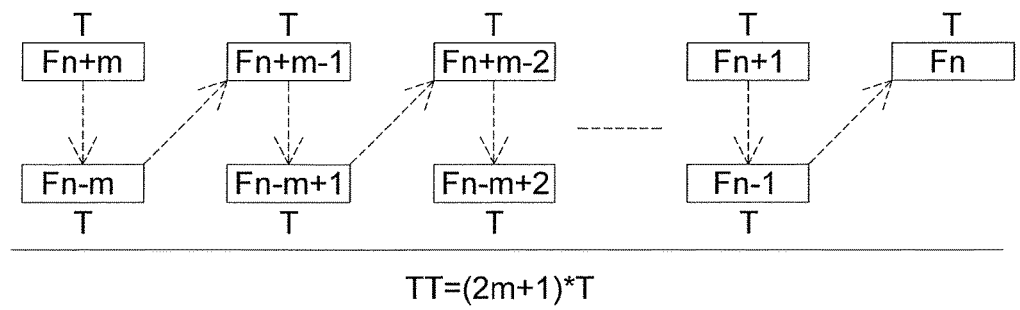
FIG. 6 is a schematic view of distribution of effect frequencies calculated by the spread contract mode of the present invention.

Referring to FIGS. 6 and 7, the control of the aforementioned spread contract mode is to control the system to emit the energy wave by alternating increasing frequency and decreasing frequency distribution with an adjusted bandwidth in a predetermined bandwidth. The calculation of the value change of the spread contract mode depicted in the present invention is described as below. The first output frequency is calculated as a base frequency (Fn) minus a sweep bandwidth (m), the second output frequency is calculated as a base frequency (Fn) plus a sweep bandwidth (m), the third output frequency is calculated as the first output frequency plus an adjusted bandwidth (such as 1 Hz), the fourth output frequency is calculated as the second output frequency minus an adjusted bandwidth (such as 1 Hz), and so on. When the current output frequency is equal to the base frequency (Fn), the current output frequency will be the last output frequency. In the case of the seventh frequency, the base frequency is 2007 Hz with sweep bandwidth (Width) (m) 7 Hz and adjusted bandwidth 1 Hz. Based on the above formula, fifteen frequencies can be obtained, and the sequence of the output frequency is 2014 Hz, 2000 Hz, 2013 Hz, 2001 Hz, 2012 Hz, 2002 Hz, 2011 Hz, 2003 Hz, 2010 Hz, 2004 Hz, 2009 Hz, 2005 Hz, 2008 Hz, 2006 Hz and 2007 Hz respectively. Each single-frequency's treatment time (T) is 2 seconds, so that the total time of the fifteen frequencies (TT) is 30 seconds, i.e., $TT=(2m+1)*T$.

Figure 8:
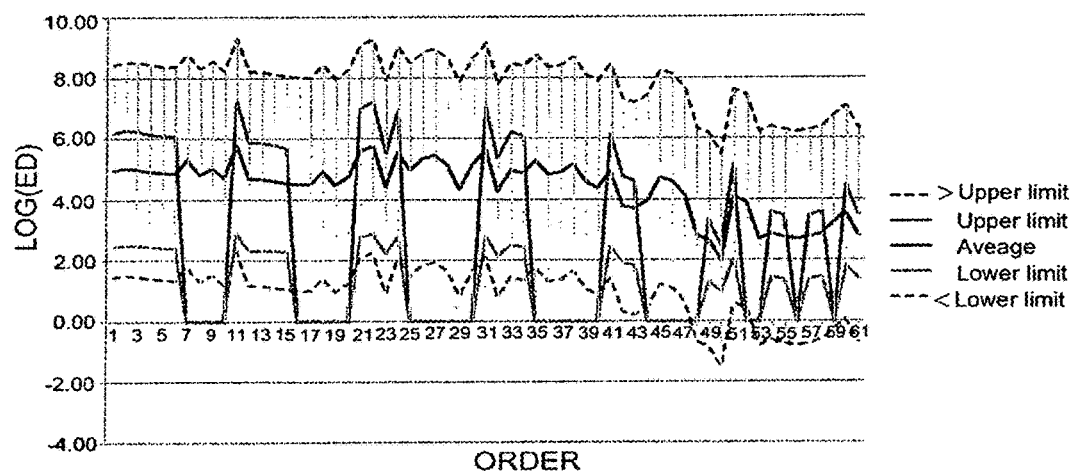
FIG. 8 is a schematic view of distribution of energy density on linear timeline of the present invention.
Figure 9:
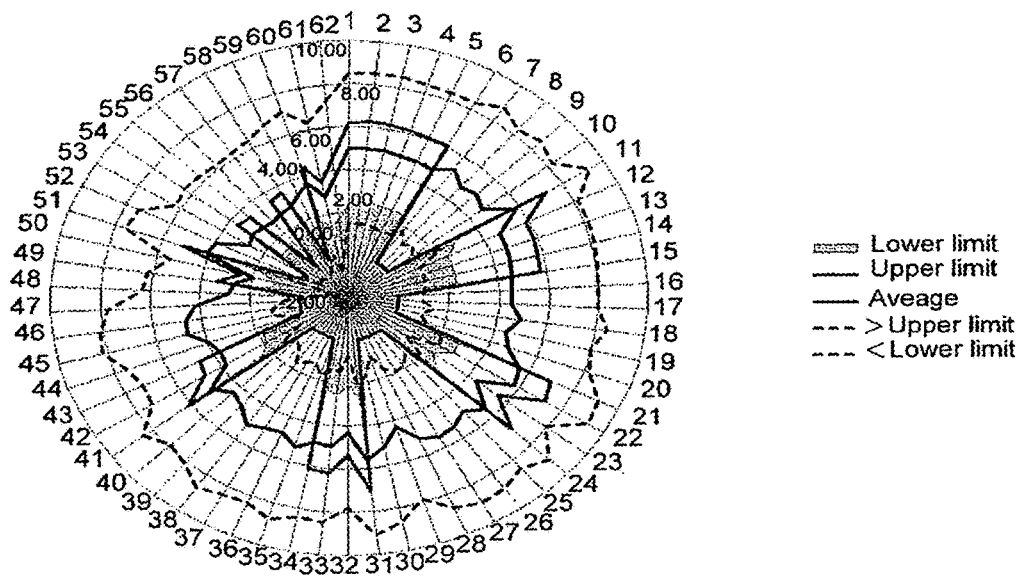
FIG. 9 is a schematic view of distribution of energy density on circular timeline of the present invention.
Figure 10:
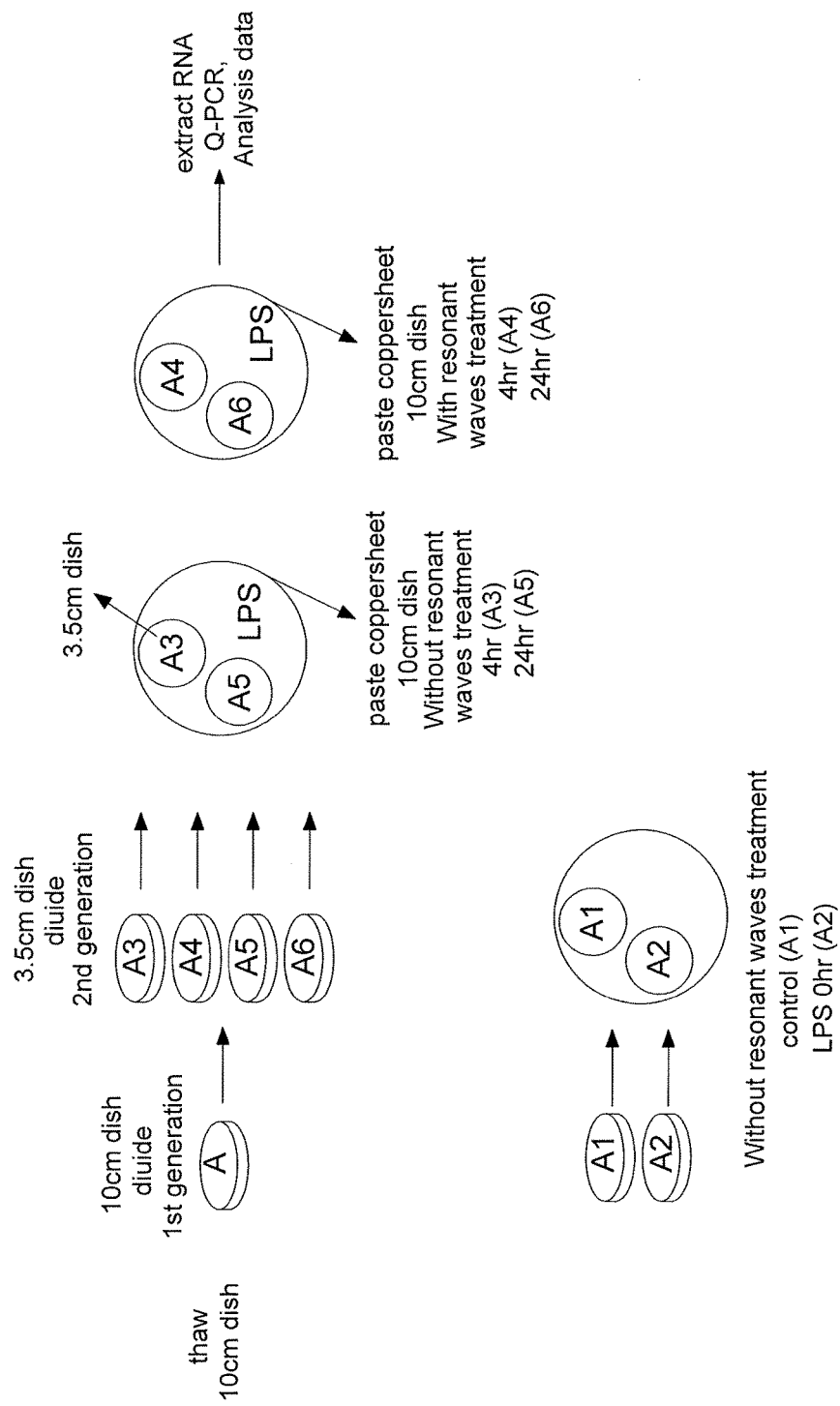
FIG. 10 is a schematic view of experimental structure of the present invention.
Figure 11:
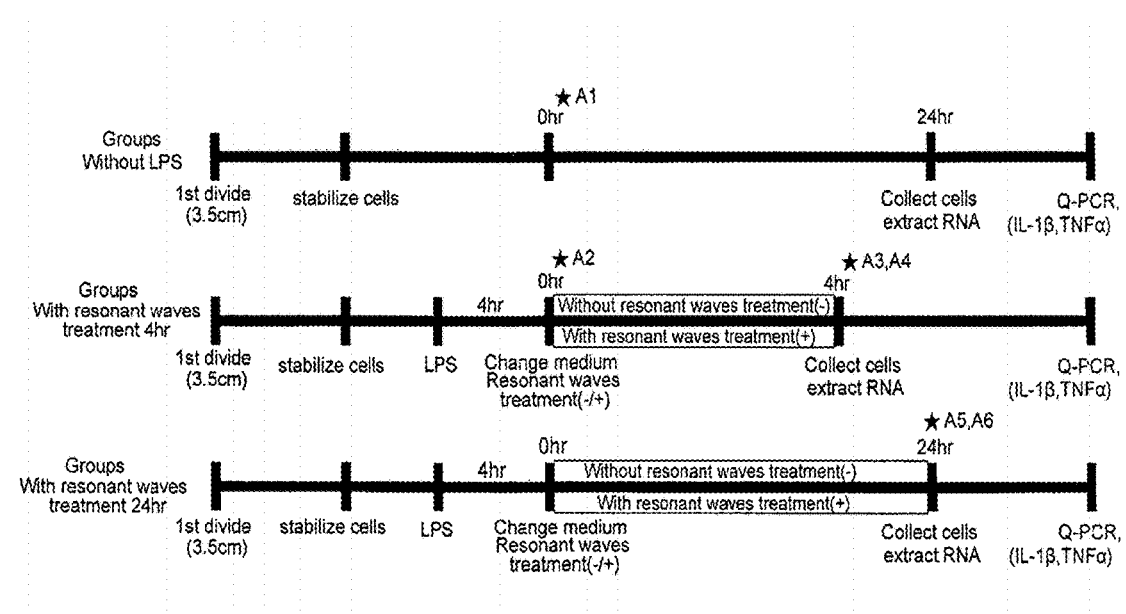
FIG. 11 is a schematic view of relations between with/without resonant energy waves treatment and time in the experiment of the present invention.

FIG. 8 shows the distribution schematic of the energy density in energy wave's frequency control mode against the linear timeline in the present invention. Wherein, the upper limit and the lower limit shown in FIG. 8 represent the upper range and the lower range of the energy density against the timeline mentioned above in accordance with the present invention. FIG. 9 shows the distribution schematic of the energy density in energy wave's frequency control mode against the annular timeline in the present invention. Wherein, the central portion is the average distribution of the energy density against the timeline mentioned above in accordance with the present invention.

On the chart shown in FIG. 7, the frequency distributions of first to ninth energy wave generation periods are from orders 1-6, 11-15, 21-24, 31-34, 41-43, 49-51, 54-55, 57-58 and 60-61 chronologically respectively. In the present embodiment, besides above frequency treatment period, the energy wave's frequency control mode also includes eight non-energy periods, i.e., from the first to the eighth non-energy periods generated between every two adjacent energy density from the first to the ninth periods correspondingly. The total time of the first to eighth non-energy periods are 132, 227, 316, 360, 449, 96, 144 and 36 seconds respectively. The energy wave generator 10 generates various frequencies in each non-energy periods and filters the frequency to have non-energy. Referring to FIG. 4, the first to the eighth non-energy periods is chronologically generated in-between order 7-10, order 16-20, order 25-30, order 35-40, order 44-48, order 52-53, order 56 and order 59 in sequence.

In order to verify the feasibility of the present invention, the applicant carry out experimental examples for oral cells as shown in FIGS. 10 to 17, the experimental material is human gingivalis fibroblasts (first generation cells). In one specific experiment, we thaw the cells in 10 cm petri dish, then divide into six groups of second generation each in 3.5 cm petri dish respectively as: group A1: Control (0 h w/o LPS); group A2: 0 h (w/LPS); group A3: 4 h w/o bRW; group A4: 4 h w/bRW; group A5: 24 h w/o bRW; and group A6: 24 h w/bRW. Wherein, groups A1 without LPS and A2 with LPS and both without resonant energy waves treatment (w/o bRW). Groups A3 with LPS and A5 with LPS are placed in 10 cm dish pasted with copper sheet and both without resonant energy waves treatment (w/o bRW). Groups A4 with LPS and A6 with LPS are placed in 10 cm dishes pasted with copper sheet respectively and both with resonant energy waves treatment (w/bRW). Those groups are extracted RNA and proceeded with Q-PCR.

Pro-inflammatory cytokines such as TNF-α, IL-β and Anti-inflammatory cytokines such as IL-10, IL-6 are collected at different time. The secretion of IL-10 can inhibit the secretion of IL-6. Number of cytokines, properties of the subject cells, properties of activation signal, properties of subsequent generation cytokines, the operation sequence of cytokines and experimental models, will significantly affect the characteristics of cytokines, so the cytokines are classified into major categories, and are determined its role in accordance with the time of collection as shown in Table 1 below.

TABLE 1

| Group | | LPS 4 hr (10 µg/ml) | Resonant wave treatment 4 hr | Resonant wave treatment 24 hr |
|---|---|---|---|---|
| No Resonant wave treatment | A1 | − | | |
| | A2 | + | | |
| Resonant wave treatment 4 hr | A3 | + | − | |
| | A4 | + | + | |
| Resonant wave treatment 24 hr | A5 | + | − | − |
| | A6 | + | + | + |

Figure 12:
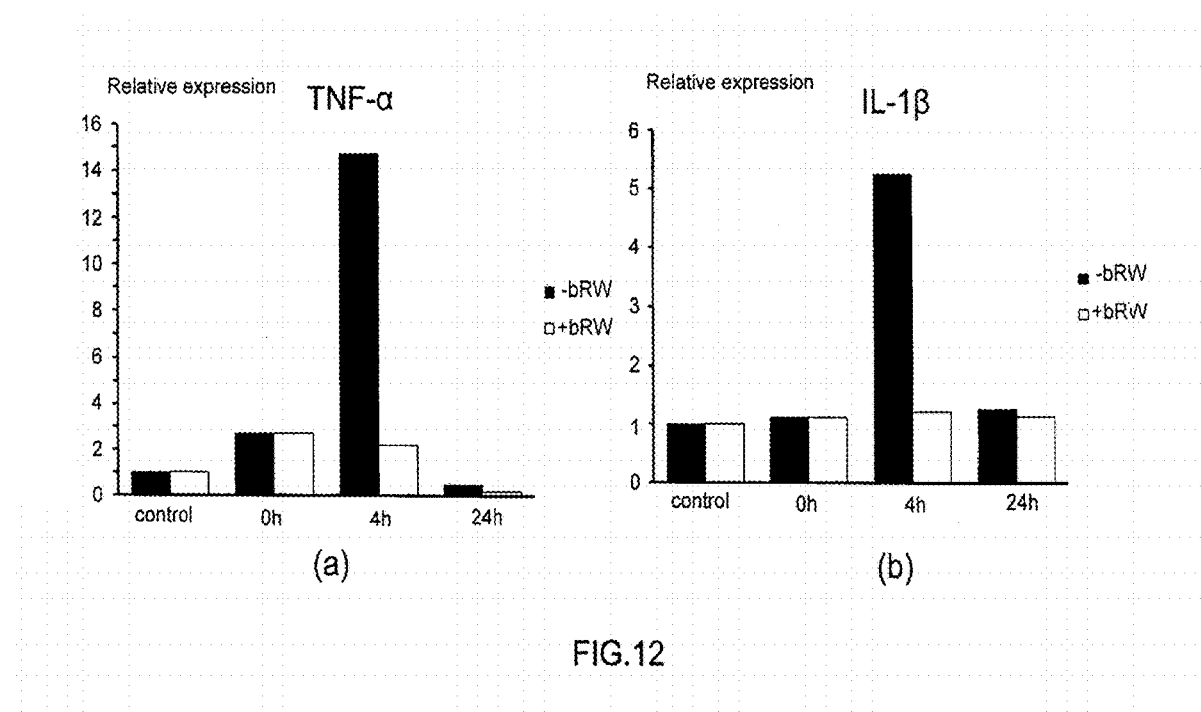
FIG. 12 is a schematic view of results of experimental example 1 of the present invention.

Referring to FIG. 12, in the experimental example 1 of the present invention, we analysis the effect of resonant energy waves on human gingivalis fibroblasts, after 4 hours and 24 hours of resonant energy waves treatment, we use real-time PCR assay gene expression, and derive the results shown as FIG. 12. Part (a) of FIG. 12 shows the status of TNF-α (tumor necrosis factor α), black tile is the TNF-α index of the group without resonant wave treatment, white tile is the TNF-α index of the group with resonant wave treatment, and those TNF-α index are the relative quantification with respect to the TNF-α index value of 1.0 of the group A1 (control). Part (b) of FIG. 12 shows the status of IL-1β (lymphocyte stimulator), black tile is the IL-1β index without resonant wave treatment, and white tile is the IL-1β index with resonant wave treatment, and those IL-1β index are the relative quantification with respect to the IL-1β index value of 1.0 of the group A1 (control).

Figure 13:
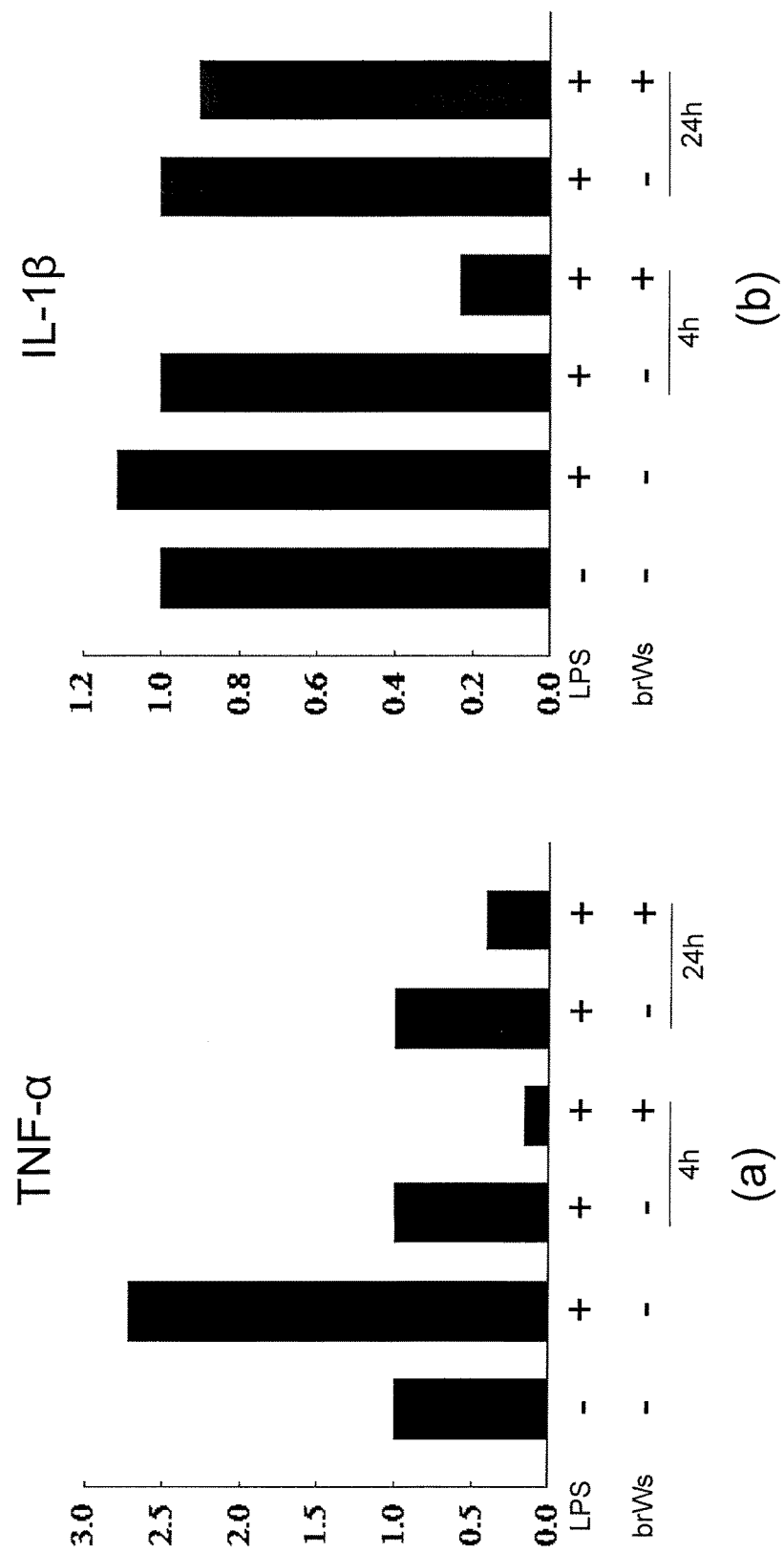
FIG. 13 is a schematic view of results of experimental example 2 of the present invention.

Referring to FIG. 13, in the experimental example 2 of the present invention, we analysis the effect of resonant energy waves on human gingivalis fibroblasts, after 4 hours and 24 hours of resonant energy waves treatment, we use real-time PCR assay gene expression, and derive the results shown as FIG. 13. Part (a) of FIG. 13 shows TNF-α index without or with LPS and without or with resonant energy waves treatment, those index are the relative quantification with respect to the value of 1.0 of the groups without resonant energy waves treatment. Part (b) of FIG. 13 shows IL-1β index without or with LPS and without or with resonant energy waves treatment, those index are the relative quantification with respect to the value of 1.0 of the groups without resonant energy waves treatment.

Figure 14:
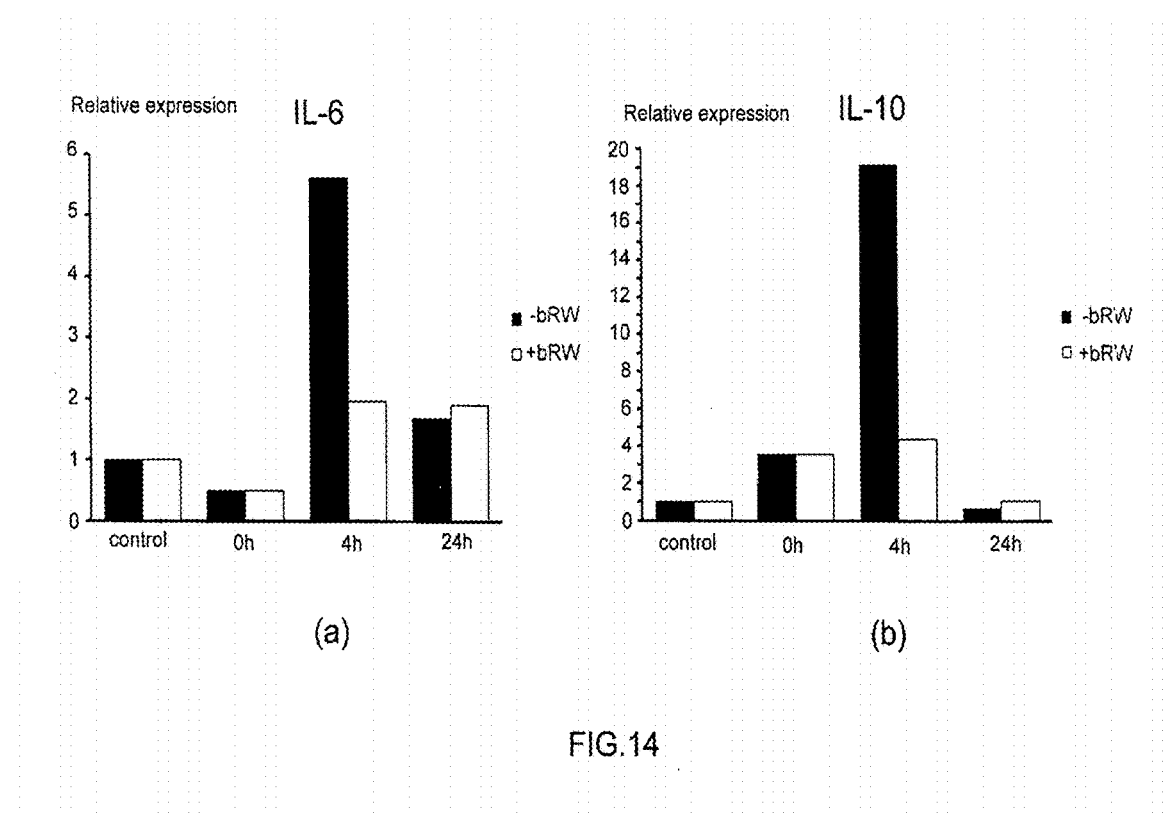
FIG. 14 is a schematic view of results of experimental example 3 of the present invention.

Referring to FIG. 14, in the experimental example 3 of the present invention, we analysis the effect of resonant energy waves on human gingivalis fibroblasts, after 4 hours and 24 hours of resonant energy waves treatment, we use real-time PCR assay gene expression, and derive the results shown as FIG. 14. Part (a) of FIG. 14 shows the status of IL-6, black tile is the IL-6 without resonant wave, white tile is the IL-6 with resonant wave treatment, and those IL-6 index are the relative quantification with respect to the value of 1.0 of the group A1 (control). Part (b) of FIG. 14 shows the status of IL-10, black tile is the IL-10 index without resonant wave treatment, and white tile is the IL-10 index with resonant wave treatment, and those IL-10 index are the relative quantification with respect to the value of 1.0 of the group A1 (control).

Figure 15:
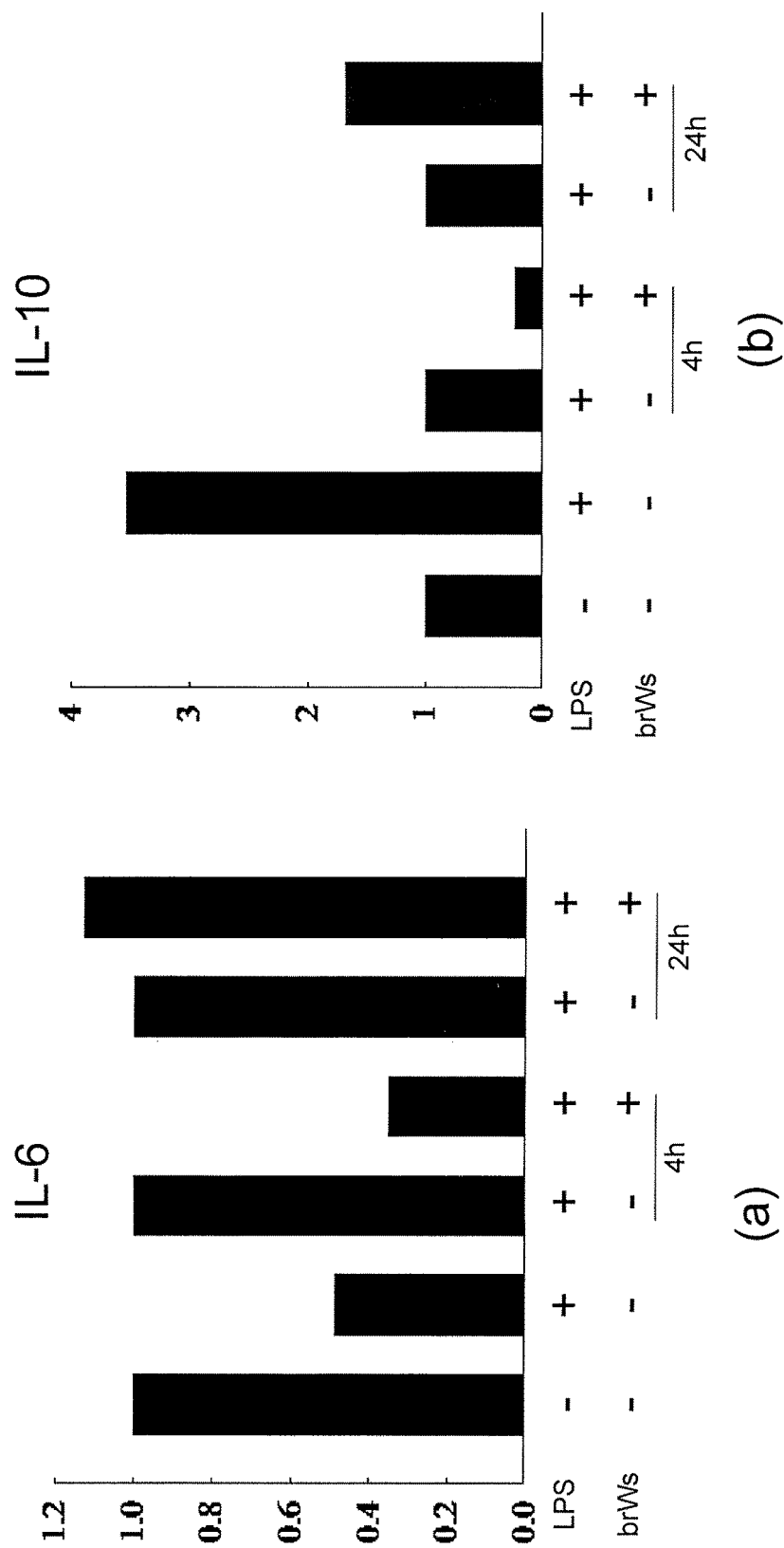
FIG. 15 is a schematic view of results of experimental example 4 of the present invention.

Referring to FIG. 15, in the experimental example 4 of the present invention, we analysis the effect of resonant energy waves on human gingivalis fibroblasts, after 4 hours and 24 hours of resonant energy waves treatment, we use real-time PCR assay gene expression, and derive the results shown as FIG. 15. Part (a) of FIG. 15 shows IL-6 index without or with LPS and without or with resonant energy waves treatment, those index are the relative quantification with respect to the value of 1.0 of the groups without resonant energy waves treatment. Part (b) of FIG. 15 shows IL-10 index without or with LPS and without or with resonant energy waves treatment, those index are the relative quantification with respect to the value of 1.0 of the groups without resonant energy waves treatment.

Figure 16:
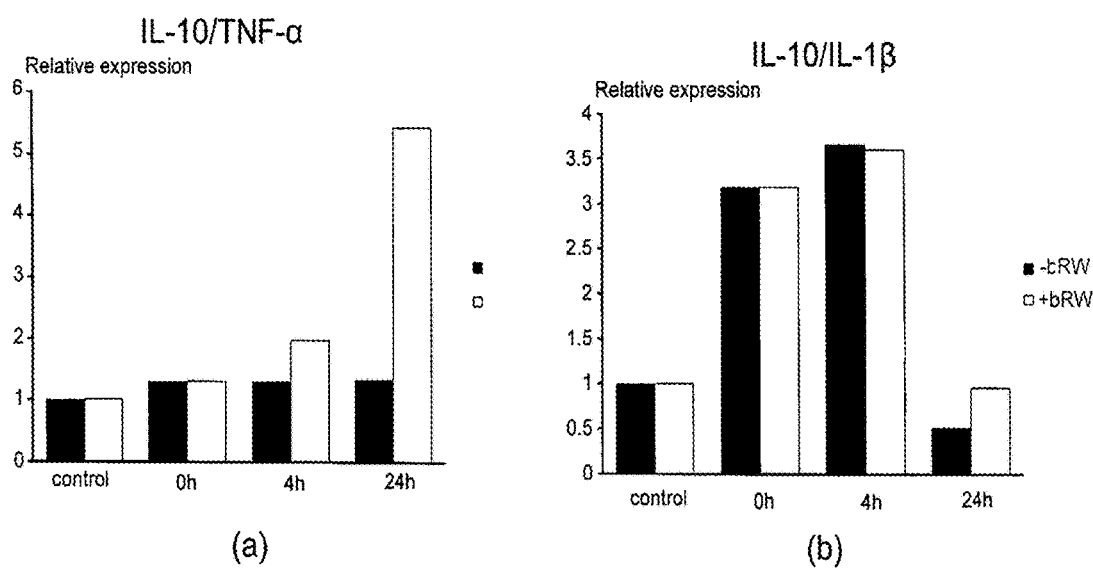
FIG. 16 is a schematic view of results of experimental example 5 of the present invention.

Referring to FIG. 16, in the experimental example 5 of the present invention, we analysis the effect of resonant energy waves on human gingivalis fibroblasts, after 4 hours and 24 hours of resonant energy waves treatment, we use real-time PCR assay gene expression, and derive the results shown as FIG. 16. Part (a) of FIG. 16 shows IL-10/TNF-α index without or with LPS and without or with resonant energy waves treatment, those index are the relative quantification with respect to the value of 1.0 of the anti-inflammatory cytokines/pro-inflammatory cytokines. Part (b) of FIG. 16 shows IL-10/IL-1β index without or with LPS and without or with resonant energy waves treatment, those index are the relative quantification with respect to the value of 1.0 of the anti-inflammatory/pro-inflammatory cytokines.

Figure 17:
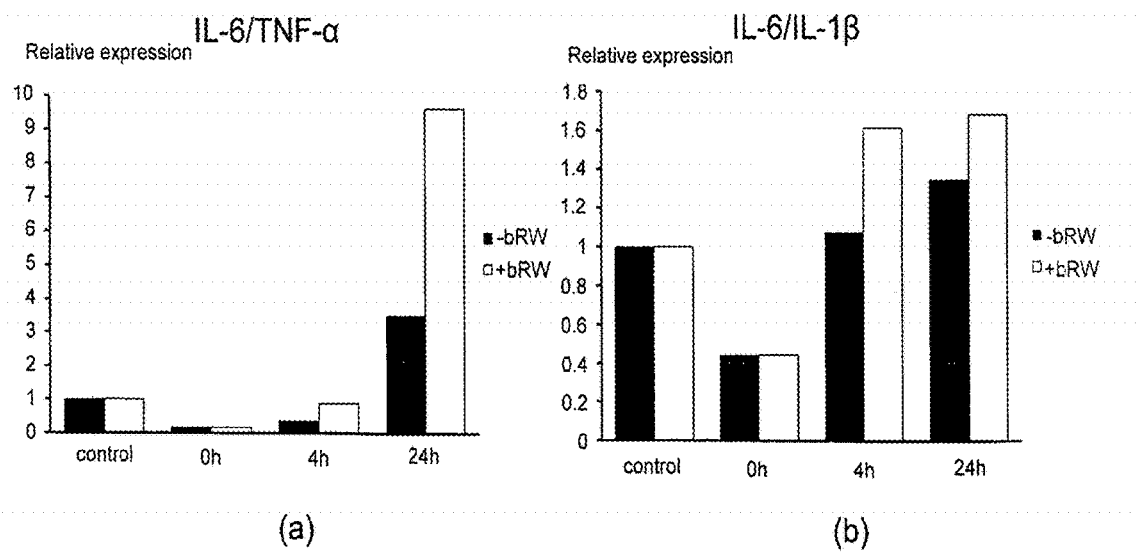
FIG. 17 is a schematic view of results of experimental example 6 of the present invention.

Referring to FIG. 17, in the experimental example 6 of the present invention, we analysis the effect of resonant energy waves on human gingivalis fibroblasts, after 4 hours and 24 hours of resonant energy waves treatment, we use real-time PCR assay gene expression, and derive the results shown as FIG. 17. Part (a) of FIG. 17 shows IL-6/TNF-α index without or with LPS and without or with resonant energy waves treatment, those index are the relative quantification with respect to the value of 1.0 of the anti-inflammatory cytokines/pro-inflammatory cytokines. Part (b) of FIG. 17 shows IL-6/IL-1β index without or with LPS and without or with resonant energy waves treatment, those index are the relative quantification with respect to the value of 1.0 of the anti-inflammatory/pro-inflammatory cytokines.

According to the results of the above experiments, we obtain the analysis information: TNF-α, IL-1β and IL-10 of group A2 are increased, IL-6 is decreased; TNF-α, IL-1β, IL-6 and IL-10 group A3 are significantly increased; IL-1β and IL-6 of group A5 are higher than the group A1 (control), and TNFα, IL-10 of group A5 are lower than the group A1 (control); TNF-α, IL-1β, IL-6 and IL-10 of group A4 are increased, but obviously much lower than A3; IL-1β and IL-6 of group A6 are higher than the group A1 (control), TNF-α of group A6 is lower than group A1 (control), IL-10 of group A6 and the group A1 (control) are equal. The result shows that the expression of IL-6 after treated with LPS is different from the expression of other cytokines. The expression of IL-6 decreases, which may be inhibited caused by secretion of IL-10. LPS promotes significantly the primary immune response (four hours), and the resonant wave treatment inhibits significantly the primary immune response. But in the later immune response (24 hours), the immune response will subside even if with or without treatment of resonant energy waves.

While we have shown and described the embodiment in accordance with the present invention, it should be clear to those skilled in the art that further embodiments may be made without departing from the scope of the present invention.

What is claimed is:

1. A system for reducing inflammation of tissue of animal or human, comprising an energy wave generator having an energy wave's frequency control mode for controlling and generating energy waves; the energy wave's frequency control mode comprising multiple controls in multiple energy wave generation periods respectively, according to the multiple controls the energy wave generator generating and emitting energy waves each with a corresponding energy density having a value between 0.99~7.25 by a corresponding base frequency between 1~18150 Hz to effect on bodies of animals or human so as to reduce inflammation of tissue of animal or human; the energy wave's frequency control mode comprising at least one fixed frequency sweep mode and at least one adjusted frequency sweep mode; the at least one adjusted frequency sweep mode being a sweep decreasing mode, a spread contract mode and/or a sweep increasing mode; the energy wave generator emitting energy waves to have a frequency decreasing distribution in a predetermined sweep bandwidth by a predetermined adjusted bandwidth in the sweep decreasing mode, to have a frequency increasing distribution in a predetermined sweep bandwidth by a predetermined adjusted bandwidth in the sweep increasing mode, and to have an increasing frequency and a decreasing frequency alternately in a predetermined sweep bandwidth by a predetermined adjusted bandwidth in the spread contract mode; the energy density of each energy wave being calculated by the following formula: ED=log 10 (freq.×D %×(2Width+1)×(TT)+1), wherein freq., Width, D % and TT represent the base frequency, the predetermined sweep bandwidth, an emission rate and a total time of emission in a duty cycle of the base frequency respectively.

2. The system as claimed in claim 1, wherein there is at least one non-energy period between every two adjacent periods of the multiple energy wave generation periods, the energy wave generator generates at least one base frequency in each non-energy period and filters the at least one base frequency to have non-energy.

3. The system as claimed in claim 1, wherein according to the multiple controls the energy wave generator in two energy wave generation periods sequentially outputs two sets of energy waves with corresponding two sets of energy densities between 2.43~6.28 and 1.41~4.48 respectively.

4. The system as claimed in claim 3, wherein the D %=70%, the Width is 0, 2 or 8 Hz, and the TT=7, 12, 15, 19, 24, 26, 28 or 36 secs; the base frequencies are between 18100~18150 Hz, 9990~10100 Hz, 7300~7370 Hz, 4990~5050 Hz, 4100~4250 Hz, 3600~3700 Hz, 10~30 Hz or 15~40 Hz.

5. The system as claimed in claim 1, wherein according to the multiple controls the energy wave generator in the multiple energy wave generation periods sequentially outputs multiple sets of energy waves with corresponding multiple sets of energy densities between 2.43~6.28, 2.21~7.21, 1.85~6.15, 1.39~3.62 and 1.41~4.48 respectively.

6. The system as claimed in claim 5, wherein the D %=70%, the Width is 0, 2, 6, 7, 8 or 9 Hz, and the TT=7, 12, 15, 19, 24, 26, 28, 36, 45, 49, 57, 65, 72, 76, 110, 133 or 144 secs; the base frequencies are between 18100~18150 Hz, 9990~10100 Hz, 7300~7370 Hz, 4990~5050 Hz, 4100~4250 Hz, 3600~3700 Hz, 800~860 Hz, 750~800 Hz, 700~790 Hz, 700~750 Hz, 130~150 Hz, 110~140 Hz, 80~110 Hz, 5~15 Hz, 5~20 Hz, 10~30 Hz or 15~40 Hz.

7. The system as claimed in claim 1, wherein the multiple controls are nine sets, the multiple energy wave generation periods are nine sequentially from a 1st to ninth corresponding to the nine sets of controls, according to the nine sets of controls the energy wave generator sequentially outputs nine sets of energy waves from a 1st to ninth with corresponding nine sets of energy densities between 2.43~6.28, 2.28~7.25, 2.21~7.21, 2.14~7.02, 1.85~6.15, 0.99~5.13, 1.39~3.62, 1.39~3.62 and 1.41~4.48 respectively.

8. The system as claimed in claim 7, wherein there are eight non-energy periods from a first to an eighth non-energy periods sequentially between every two adjacent periods of the multiple energy wave generation periods, the energy wave generator generates various frequencies in each non-energy period and filters the various frequencies to have non-energy correspondingly.

9. The system as claimed in claim 8, wherein the total time of the first to eighth non-energy periods are 132, 227, 316, 360, 449, 96, 144 and 36 seconds respectively, the energy wave generator generates various frequencies in each non-energy period and filters the various frequencies to have non-energy.

10. The system as claimed in claim 7, wherein in the first energy wave generation period corresponding to the first set of controls, the first sets of energy waves are sequentially a 1st to a 6th energy waves with a 1st to a 6th energy densities by a 1st to a 6th base frequencies respectively, the 1st energy density is between 2.47~6.19, the 2nd energy density is between 2.51~6.28, the 3rd energy density is between 2.49~6.24, the 4th energy density is between 2.46~6.16, the 5th energy density is between 2.44~6.10, and the 6th energy density is between 2.43~6.07; in the second energy wave generation period corresponding to the second set of controls, the second sets of energy waves are sequentially a 7th to a 11th energy waves with corresponding a 7th to a 11th energy densities by a 7th to a 11th base frequencies respectively, the 7th energy density is between 2.90~7.25, the 8th energy density is between 2.34~5.85, the 9th energy density is between 2.34~5.85, the 10th energy density is between 2.31~5.78, the 11th energy density is between 2.28~5.70; in the third energy wave generation period corresponding to the third set of controls, the third sets of energy waves are sequentially a 12th to a 15th energy waves with a 12th to a 15th energy densities by a 12th to a 15th base frequencies respectively, the 12th energy density is between 2.79~6.98, the 13th energy density is between 2.89~7.21, the 14th energy density is between 2.21~5.51, the 15th energy density is between 2.77~6.92; in the fourth energy wave generation period corresponding to the fourth set of controls, the fourth sets of energy waves are sequentially a 16th to a 19th energy waves with a 16th to a 19th energy densities by a 16th to a 19th base frequencies respectively, the 16th energy density is between 2.81~7.02, the 17th energy density is between 2.14~5.36, the 18th energy density is between 2.48~6.21, the 19th energy density is between 2.43~6.07; in the fifth energy wave generation period corresponding to the fifth set of controls, the fifth sets of energy waves are sequentially a 20th to a 22nd energy waves with a 20th to a 22nd energy densities by a 20th to a 22nd base frequencies respectively, the 20th energy density is between 2.46~6.15, the 21st energy density is between 1.90~4.75, the 22nd the energy density is between 1.85~4.63; in the sixth energy wave generation period corresponding to the sixth set of controls, the sixth sets of energy waves are sequentially a 23rd to a 25th energy waves with a 23rd to a 25th energy densities by a 23rd to a 25th base frequencies respectively, the 23rd energy density is between 1.33~3.33, the 24th energy density is between 0.99~2.47, the 25th energy density is between 2.05~5.13; in the seventh energy wave generation period corresponding to the seventh set of controls, the seventh sets of energy waves are sequentially a 26th to a 27th energy waves with a 26th to a 27th energy densities by a 26th to a 27th base frequencies respectively, the 26th energy density is between 1.45~3.62, the 27th energy density is between 1.39~3.48; in the eighth energy wave generation period corresponding to the eighth set of controls, the eighth sets of energy waves are sequentially a 28th to a 29th energy waves with a 28th to a 29th energy densities by a 28th to a 29th base frequencies respectively, the 28th energy density is between 1.39~3.48, the 29th energy density is between 1.45~3.62; and in the ninth energy wave generation period corresponding to the ninth set of controls, the ninth sets of energy waves are sequentially a 30th to a 31st energy waves with a 30th to a 31st energy densities by a 30th to a 31st base frequencies respectively, the 30th energy density is between 1.79~4.48, and the 31st energy density is between 1.41~3.52.

11. The system as claimed in claim 10, wherein in the controls based on the 1st to 6th, 8th to 11th, 14th, 17th, 21st to 24th, 26th to 29th base frequencies, the D %=70%, the Width=0 Hz, and the TT=7, 15, 19, 24, 26, 28, 37, 37, 39, 42, 49, 53, 72, 76, 110, 133, 144, 144, 144 and 144 secs respectively; in the controls based on the 19th and 25th base frequencies, the D %=70%, the Width=3 and 8 Hz, and the TT=56 and 72 secs respectively; in the controls of the 18th, 30th and 31st base frequencies, the D %=70%, the Width=4, 8 and 2 Hz respectively, and the TT=55, 36 and 12 secs respectively; in the controls based on the 7th, 12th, 13th, 15th, 16th and 20th base frequencies, the D %=70%, the Width=7, 7, 9, 7, 9 and 6 Hz, and the TT=30, 45, 57, 45, 57 and 65 secs respectively; the 1st to 39th base frequencies are between 18100~18150 Hz, 9990~10100 Hz, 7300~7370 Hz, 4990~5050 Hz, 4100~4250 Hz, 3600~3700 Hz, 2000~2080 Hz, 1800~1900 Hz, 1830~1860 Hz, 1500~1590 Hz, 1220~1250 Hz, 800~860 Hz, 750~800 Hz, 700~790 Hz, 700~750 Hz, 500~580 Hz, 510~550 Hz, 470~500 Hz, 450~480 Hz, 130~150 Hz, 110~140 Hz, 80~110 Hz, 4~10 Hz, 0.5~10 Hz, 20~50 Hz, 5~20 Hz, 5~15 Hz, 5~15 Hz, 5~20 Hz, 10~30 Hz and 15~40 Hz respectively.

12. The system as claimed in claim 11, wherein modes of the controls based on the 1st to 6th, 8th to 11th, 14th, 17th, 21st to 24th, and 26th to 29th base frequencies are fixed frequency sweep modes respectively; modes of the controls based on the 23rd and 29th base frequencies are sweep decreasing modes respectively, multiple frequencies being produced and calculated by one predetermined adjusted bandwidth based on each base frequency in each sweep decreasing mode; modes of the controls based on the 7th, 12th, 13th 15th, 16th and 20th base frequency are spread contract modes respectively, multiple frequencies being produced and calculated by one predetermined adjusted bandwidth based on each base frequency in each spread contract mode; modes of the controls based on the 18th, 30th and 31st base frequencies are sweep increasing modes respectively, multiple frequencies being produced and calculated by one predetermined adjusted bandwidth based on each base frequency in each sweep increasing mode; in the sweep decreasing mode, the first output frequency of the multiple frequencies is calculated as the base frequency plus the Width, the second output frequency of the multiple frequencies is calculated as the first output frequency minus the predetermined adjusted bandwidth, and when a current output frequency of the multiple frequencies is equal to the base frequency, the current output frequency is a last output frequency; in the spread contract mode, the first output frequency of the multiple frequencies is calculated as the base frequency minus the Width, the second output frequency of the multiple frequencies is calculated as a base frequency plus the Width, the third output frequency of the multiple frequencies is calculated as the first output frequency plus the predetermined adjusted bandwidth, the fourth output frequency of the multiple frequencies is calculated as the second output frequency minus the predetermined adjusted bandwidth and so on, and when the current output frequency of the multiple frequencies is equal to the base frequency, the current output frequency is the last output frequency; in the sweep increasing mode, the first output frequency of the multiple frequencies is calculated as the base frequency minus the sweep bandwidth, the second output frequency of the multiple frequencies is calculated as the first output frequency plus the predetermined adjusted bandwidth, and when the current output frequency of the multiple frequencies is equal to the base frequency, the current output frequency is the last output frequency.

13. The system as claimed in claim 12, wherein the predetermined adjusted bandwidths in the sweep decreasing modes, the spread contract mode and the sweep increasing mode are equal to 1 Hz respectively.

14. A method for reducing inflammation of tissue of animal or human, comprising the steps of:
providing a system, the system comprising an energy wave generator having an energy wave's frequency control mode for controlling and generating energy waves; the energy wave's frequency control mode comprising multiple controls in multiple energy wave generation periods respectively; the energy wave's frequency control mode comprising at least one fixed frequency sweep mode and at least one adjusted frequency sweep mode; the at least one adjusted frequency sweep mode being a sweep decreasing mode, a spread contract mode and/or a sweep increasing mode; the energy waves having a frequency decreasing distribution in a predetermined sweep bandwidth by a predetermined adjusted bandwidth in the sweep decreasing mode, having a frequency increasing distribution in a predetermined sweep bandwidth by a predetermined adjusted bandwidth in the sweep increasing mode, and having an increasing frequency and a decreasing frequency alternately in a predetermined sweep bandwidth by a predetermined adjusted bandwidth in the spread contract mode; the energy density of each energy wave being calculated by the following formula: ED=log 10 (freq.×D %×(2Width+1)×(TT)+1), wherein freq., Width, D % and TT represent the base frequency, the predetermined sweep bandwidth, an emission rate and a total time of emission in a duty cycle of the base frequency respectively, and
driving the energy wave generator according to the multiple controls to generate and emit energy waves each with a corresponding energy density having a value between 0.99~7.25 by a corresponding base frequency between 1~18150 Hz to effect on bodies of animals or human so as to reduce inflammation of tissue of animal or human.

15. The method as claimed in claim 14, wherein the multiple controls are nine sets, the multiple energy wave generation periods are nine sequentially from a 1st to ninth corresponding to the nine sets of controls, according to the nine sets of controls the energy wave generator sequentially outputs nine sets of energy waves from a 1st to ninth with corresponding nine sets of energy densities between 2.43~6.28, 2.28~7.25, 2.21~7.21, 2.14~7.02, 1.85~6.15, 0.99~5.13, 1.39~3.62, 1.39~3.62 and 1.41~4.48 respectively.

16. The method as claimed in claim 15, wherein there are eight non-energy periods from a first to an eighth non-energy periods sequentially between every two adjacent periods of the multiple energy wave generation periods, the energy wave generator generates various frequencies in each non-energy period and filters the various frequencies to have non-energy correspondingly.

17. The method as claimed in claim 16, wherein the total time of the first to eighth non-energy periods are 132, 227, 316, 360, 449, 96, 144 and 36 seconds respectively, the energy wave generator generates various frequencies in each non-energy period and filters the various frequencies to have non-energy.

18. The method as claimed in claim 15, wherein in the first energy wave generation period corresponding to the 1st set of controls, the first sets of energy waves are sequentially a 1st to a 6th energy waves with a 1st to a 6th energy densities by a 1st to a 6th base frequencies respectively, the 1st energy density is between 2.47~6.19, the 2nd energy density is between 2.51~6.28, the 3rd energy density is between 2.49~6.24, the 4th energy density is between 2.46~6.16, the 5th energy density is between 2.44~6.10, and the 6th energy density is between 2.43~6.07; in the second energy wave generation period corresponding to the second set of controls, the second sets of energy waves are sequentially a 7th to a 11th energy waves with corresponding a 7th to a 11th energy densities by a 7th to a 11th base frequencies respectively, the 7th energy density is between 2.90~7.25, the 8th energy density is between 2.34~5.85, the 9th energy density is between 2.34~5.85, the 10th energy density is between 2.31~5.78, the 11th energy density is between 2.28~5.70; in the third energy wave generation period corresponding to the third set of controls, the third sets of energy waves are sequentially a 12th to a 15th energy waves with a 12th to a 15th energy densities by a 12th to a 15th base frequencies respectively, the 12th energy density is between 2.79~6.98, the 13th energy density is between 2.89~7.21, the 14th energy density is between 2.21~5.51, the 15th energy density is between 2.77~6.92; in the fourth energy wave generation period corresponding to the fourth set of controls, the fourth sets of energy waves are sequentially a 16th to a 19th energy waves with a 16th to a 19th energy densities by a 16th to a 19th base frequencies respectively, the 16th energy density is between 2.81~7.02, the 17th energy density is between 2.14~5.36, the 18th energy density is between 2.48~6.21, the 19th energy density is between 2.43~6.07; in the fifth energy wave generation period corresponding to the fifth set of controls, the fifth sets of energy waves are sequentially a 20th to a 22nd energy waves with a 20th to a 22nd energy densities by a 20th to a 22nd base frequencies respectively, the 20th energy density is between 2.46~6.15, the 21st energy density is between 1.90~4.75, the 22nd the energy density is between 1.85~4.63; in the sixth energy wave generation period corresponding to the sixth set of controls, the sixth sets of energy waves are sequentially a 23rd to a 25th energy waves with a 23rd to a 25th energy densities by a 23rd to a 25th base frequencies respectively, the 23rd energy density is between 1.33~3.33, the 24th energy density is between 0.99~2.47, the 25th energy density is between 2.05~5.13; in the seventh energy wave generation period corresponding to the seventh set of controls, the seventh sets of energy waves are sequentially a 26th to a 27th energy waves with a 26th to a 27th energy densities by a 26th to a 27th base frequencies respectively, the 26th energy density is between 1.45~3.62, the 27th energy density is between 1.39~3.48; in the eighth energy wave generation period corresponding to the eighth set of controls, the eighth sets of energy waves are sequentially a 28th to a 29th energy waves with a 28th to a 29th energy densities by a 28th to a 29th base frequencies respectively, the 28th energy density is between 1.39.3.48, the 29th energy density is between 1.45~3.62; and in the ninth energy wave generation period corresponding to the ninth set of controls, the ninth sets of energy waves are sequentially a 30th to a 31st energy waves with a 30th to a 31st energy densities by a 30th to a 31st base frequencies respectively, the 30th energy density is between 1.79~4.48, and the 31st energy density is between 1.41~3.52.

19. The method as claimed in claim 18, wherein in the controls based on the 1st to 6th, 8th to 11th, 14th, 17th, 21st to 24th, 26th to 29th base frequencies, the D %=70%, the Width=0 Hz, and the TT=7, 15, 19, 24, 26, 28, 37, 37, 39, 42, 49, 53, 72, 76, 110, 133, 144, 144, 144 and 144 secs respectively; in the controls based on the 19th and 25th base frequencies, the D %=70%, the Width=3 and 8 Hz, and the TT=56 and 72 secs respectively; in the controls of the 18th, 30th and 31st base frequencies, the D %=70%, the Width=4, 8 and 2 Hz respectively, and the TT=55, 36 and 12 secs respectively; in the controls based on the 7th, 12th, 13th, 15th, 16th and 20th base frequencies, the D %=70%, the Width=7, 7, 9, 7, 9 and 6 Hz, and the TT=30, 45, 57, 45, 57 and 65 secs respectively; the 1st to 39th base frequencies are between 18100~18150 Hz, 9990~10100 Hz, 7300~7370 Hz, 4990~5050 Hz, 4100~4250 Hz, 3600~3700 Hz, 2000~2080 Hz, 1800~1900 Hz, 1830~1860 Hz, 1500~1590 Hz, 1220~1250 Hz, 800~860 Hz, 750~800 Hz, 700~790 Hz, 700~750 Hz, 500~580 Hz, 510~550 Hz, 470~500 Hz, 450~480 Hz, 130~150 Hz, 110~140 Hz, 80~110 Hz, 4~10 Hz, 0.5~10 Hz, 20~50 Hz, 5~20 Hz, 5~15 Hz, 5~15 Hz, 5~20 Hz, 10~30 Hz and 15~40 Hz respectively.

20. The method as claimed in claim 19, wherein modes of the controls based on the 1st to 6th, 8th to 11th, 14th, 17th, 21st to 24th, and 26th to 29th base frequencies are fixed frequency sweep modes respectively; modes of the controls based on the 23rd and 29th base frequencies are sweep decreasing modes respectively, multiple frequencies being produced and calculated by one predetermined adjusted bandwidth based on each base frequency in each sweep decreasing mode; modes of the controls based on the 7th, 12th, 13th 15th, 16th and 20th base frequency are spread contract modes respectively, multiple frequencies being produced and calculated by one predetermined adjusted bandwidth based on each base frequency in each spread contract mode; modes of the controls based on the 18th, 30th and 31st base frequencies are sweep increasing modes respectively, multiple frequencies being produced and calculated by one predetermined adjusted bandwidth based on each base frequency in each sweep increasing mode; in the sweep decreasing mode, the first output frequency of the multiple frequencies is calculated as the base frequency plus the Width, the second output frequency of the multiple frequencies is calculated as the first output frequency minus the predetermined adjusted bandwidth, and when a current output frequency of the multiple frequencies is equal to the base frequency, the current output frequency is a last output frequency; in the spread contract mode, the first output frequency of the multiple frequencies is calculated as the base frequency minus the Width, the second output frequency of the multiple frequencies is calculated as a base frequency plus the Width, the third output frequency of the multiple frequencies is calculated as the first output frequency plus the predetermined adjusted bandwidth, the fourth output frequency of the multiple frequencies is calculated as the second output frequency minus the predetermined adjusted bandwidth and so on, and when the current output frequency of the multiple frequencies is equal to the base frequency, the current output frequency is the last output frequency; in the sweep increasing mode, the first output frequency of the multiple frequencies is calculated as the base frequency minus the sweep bandwidth, the second output frequency of the multiple frequencies is calculated as the first output frequency plus the predetermined adjusted bandwidth, and when the current output frequency of the multiple frequencies is equal to the base frequency, the current output frequency is the last output frequency.

* * * * *